United States Patent
Yin et al.

(10) Patent No.: US 10,669,353 B2
(45) Date of Patent: Jun. 2, 2020

(54) PREPARATION METHOD OF OUTER CORE OCTASACCHARIDE OF HELICOBACTER PYLORI LIPOPOLYSACCHARIDE

(71) Applicants: Jiangnan University, Wuxi (CN); Max Planck Institute of Colloids and Interfaces, Potsdam (DE)

(72) Inventors: Jian Yin, Wuxi (CN); Jing Hu, Wuxi (CN); Peter Seeberger, Potsdam (DE); Xiaopeng Zou, Wuxi (CN)

(73) Assignee: Jiangnan University, Jiangsu, Wuxi (CN)

( * ) Notice: Subject to any disclaimer, the term of this patent is extended or adjusted under 35 U.S.C. 154(b) by 63 days.

(21) Appl. No.: 16/215,414

(22) Filed: Dec. 10, 2018

(65) Prior Publication Data

US 2019/0177441 A1  Jun. 13, 2019

Related U.S. Application Data

(63) Continuation of application No. PCT/CN2017/116187, filed on Dec. 14, 2017.

(30) Foreign Application Priority Data

Dec. 11, 2017 (CN) .......................... 2017 1 1304779

(51) Int. Cl.
*C08B 37/00* (2006.01)
*A61K 39/00* (2006.01)

(52) U.S. Cl.
CPC ............ *C08B 37/006* (2013.01); *A61K 39/00* (2013.01)

(58) Field of Classification Search
None
See application file for complete search history.

(56) References Cited

FOREIGN PATENT DOCUMENTS

CN  102482646 A  5/2012

OTHER PUBLICATIONS

Montiero et al., "Lipopolysaccharide structures of Helicobacter pylori genomic strains 26695 and J99, mouse model H. pylori Sydney strain, H. pylori P466 carrying sialyl Lewis X, and H. pylori UA915 expressiong Lewis B" Eur J Biochem vol. 267 pp. 305-320 (Year: 2000).*

Mario A. Monteiro, Helicobacter pylori: A Wolf in Sheep"s Clothing: The Glycotype Families of Helicobacter pylori Lipopolysaccharides Expressing Histo-Blood Groups: Structure, Biosynthesis, and Role in Pathogenesis, Advances in Carbohyradrate Chemistry and Biochemistry, Dec. 31, 2001(Dec. 31, 2001), vol. 57, pp. 99-158.

Park, Jin et al., Stereoselective Glycosylations of 2-Azido-2-deoxyglucosides Using Intermediate Sulfonium Ions, Organic Letters, Apr. 14, 2007(Apr. 14, 2007), No. 10, vol. 9, pp. 1959-1962.

Brition, Stacey et al., A novel Helicobacter pylori cell-surface polysaccharide, Carbohydrate Research, Dec. 31, 2005(Dec. 31, 2005), vol. 340, pp. 1605-1611.

Tsai, Yu-hsuan et al., A general and convergent synthesis of diverse glycosylphosphatidylinositol glycolipids, Chemical Science, Nov. 1, 2012 (Nov. 1, 2012), vol. 4, pp. 468-481.

* cited by examiner

*Primary Examiner* — Eric Olson
(74) *Attorney, Agent, or Firm* — IPro, PLLC; Na Xu

(57) ABSTRACT

The disclosure discloses a preparation method of outer core octasaccharide of *Helicobacter pylori* lipopolysaccharide, and belongs to the field of carbohydrate chemistry. The structure of the outer core octasaccharide of *Helicobacter pylori* is ($\alpha$-D-Glc-(1-3)-$\alpha$-D-Glc-(1-4)-$\beta$-D-Gal-(1-7)-D-$\alpha$-D-Hep[$\alpha$-D-Glc-(1-6)-$\alpha$-D-Glc-(1-6)-$\alpha$-D-Glc-(1-2)-D-$\alpha$-D-Hep]-Linker. The structure consists of three monosaccharides: glucose, galactose and heptose. It contains five $\alpha$-glycosidic bonds of glucose, one $\beta$-glycosidic bond of galactose and two $\alpha$-glycosidic bonds of heptose. The disclosure prepares the octasaccharide by the synergistic action of remote neighboring group participation effect, solvent effect, temperature effect, additives and leaving groups. The reducing end of the octasaccharide may also be linked with a linker for future attachment to the protein to form a glycoconjugate for immunological studies.

11 Claims, 4 Drawing Sheets

PREPARATION METHOD OF OUTER CORE OCTASACCHARIDE OF HELICOBACTER PYLORI LIPOPOLYSACCHARIDE

TECHNICAL FIELD

The present disclosure relates to a preparation method of outer core octasaccharide of *Helicobacter Pylori* lipopolysaccharide, belonging to the field of carbohydrate chemistry.

BACKGROUND

*Helicobacter Pylori* (H.P.) was classified as a Class I carcinogen by the World Health Organization in 1994. It is a Gram-negative bacterium that inhabits the surface of epithelial cells and is covered by mucus on the surface of the gastric mucosa. More than 50% of the world's population has *Helicobacter Pylori* infection in the upper gastrointestinal tract with up to 70% of infected people in developing countries, and 20% to 30% in developed countries. In acute infections, 20% of patients develop ulcers, and 1% of infected person may even develop gastric cancer or mucosa-associated lymphoma. In 2005, the Nobel Prize in Physiology or Medicine was awarded to two Australian scientists, Warren and Mashall, for their important role in discovering the effect of *H. Pylori* on digestive tract diseases and gastric cancer. The most common method for treating *H. pylori* is "triple therapy", which uses a proton pump inhibitor and two antibiotics to remove *H. pylori*. However, patients are prone to relapse after administration, and often have adverse reactions such as nausea, diarrhea, and pseudomembranous colitis. Along with the frequent use of antibiotics, antibiotic-resistant strains of *H. pylori* have been continuously discovered, which has led to a gradual decrease in the efficiency of antibiotic treatment of *H. pylori*. Therefore, the development of *H. pylori* vaccine has always been a hot spot for scientists.

There are no vaccines on the market that prevent *H. pylori* infection or treat *H. pylori* currently. As a new target molecule for vaccine development, carbohydrate vaccines attract more and more attention by scientists. The polysaccharide structure on the surface of bacteria often plays an important role in the pathogenicity of bacteria and immune recognition in human body. Therefore, chemical synthesis of *H. pylori* surface oligosaccharides is of great significance to the development of *H. pylori* vaccine.

The oligosaccharide on the surface of *H. pylori* cells is Lipopolysaccharide (LPS). This LPS consists of O-antigen, core structure, and lipid A. There are a total of 6 serotypes for *H. pylori*, O1-O6, and the difference between them is mainly the difference in the O-antigen sugar moiety. The core structure of LPS for different serotypes of *H. pylori* is relatively conservative, so it is a good choice to chemically synthesize its core structure for use as a carbohydrate vaccine for the prevention and treatment of *H. pylori* infection. The core structure of *H. pylori* includes the inner core and the outer core. The latter is more likely to be exposed to the environment, and plays a very important role in the in vivo immune response caused by *H. pylori* infection.

The core structure of *H. pylori* lipopolysaccharide currently studied is mainly extracted from inactivated bacteria by biological methods. The defect is that the amount of product obtained by one extraction is usually small, the molecular structures obtained from extraction are not uniform, and the experimental repeatability is poor. Therefore, we selected the outer core octasaccharide of *H. pylori* as our target molecules for the chemical total synthesis. Through chemical synthesis, we can obtain a large number of target molecules with uniform and defined structures.

SUMMARY

The technical problem to be solved by the present disclosure is to synthesize an outer core octasaccharide of *H. pylori* by a chemical method. This octasaccharide structure has five glucoses, and the synthesis of α-1,2-glycosidic bonds is a key step for synthesis of the target octasaccharide. The disclosure utilizes the synergistic action of remote neighboring group participation effect, solvent effect, temperature effect, additive and leaving group to improve the α-selectivity during the glycosylation process. This synergistic solution successfully solves the problem of the formation of α-glycosidic bond of glucose. A final protected target octasaccharide is synthesized using the synthetic glucose building block, galactose building block, and heptose building block, and then the protection is removed to obtain the target octasaccharide as shown in Formula I. At the same time, the reducing end of the octasaccharide is a linker with an amino group, which can bind with protein to prepare a glycoconjugate vaccine.

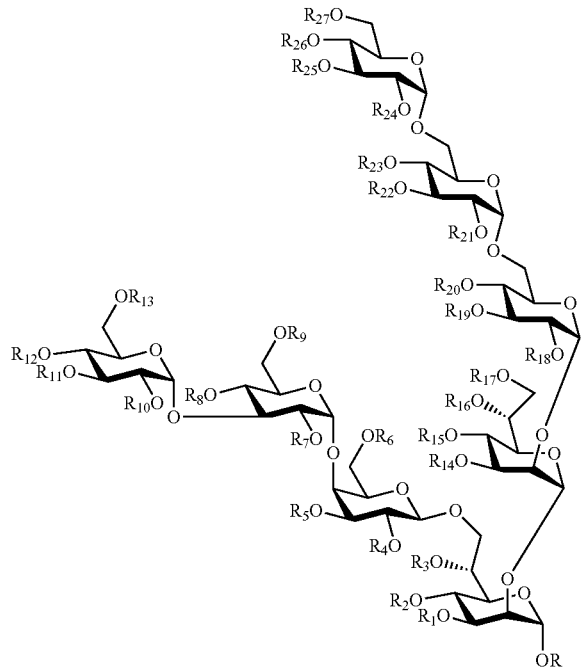

Formula I wherein, R is —$(CH_2)_n$—N—$Y_1Y_2$ or —$(CH_2)_n$—N—$Y_1Y_2$ (linker), n=1-10, $Y_1$ is H or benzyl (Bn), $Y_2$ is H or carbobenzoxy (Cbz). $R_1$, $R_2$, $R_3$, $R_6$, $R_7$, $R_8$, $R_{10}$, $R_{12}$, $R_{14}$, $R_{15}$, $R_{16}$, $R_{18}$, $R_{20}$, $R_{21}$, $R_{23}$, $R_{24}$, and $R_{26}$ are H or benzyl (Bn); $R_5$, $R_{11}$, $R_{17}$, $R_{19}$, $R_{22}$, and $R_{25}$ is H or 2-naphthylmethyl (Nap); $R_4$, $R_9$, $R_{13}$, and $R_{27}$ are ester groups. N is nitrogen.

The disclosure also provides a method for synthesizing the compound of Formula I, which specifically comprises the following steps:

Step 1, a glucose building block A is synthesized. The structure of the sugar building block A is as shown in Formula II, the terminal group is N-phenyl-trifluoroacetimidate as a leaving group, and the remaining substituents $R_n$ are shown in the Formula I.

Specifically, the method for synthesizing the monosaccharide building block A comprises: using peracetylated glucose as a starting material, reacting it with p-thiocresol under the action of a Lewis acid to form a peracetylthioglycoside compound, and deacetylating under an alkaline condition to expose four hydroxy groups. The obtained tetrahydroxy compound with benzaldehyde dimethyl acetal (PhCH(OCH$_3$)$_2$) via the catalysis of p-toluenesulfonic acid (p-TsOH.H$_2$O) to form a 4,6-benzylidene-protected thioglycoside compound; protecting the 3-OH of the 4,6-benzylidene-protected thioglycoside compound with 2-methylnaphthalene (2-Nap), protecting the 2-OH with benzyl (Bn) to obtain a fully protected compound, after that, selectively opening the 4,6-benzylidene under the action of borane (BH$_3$.THF) and a Lewis acid to expose the 6-OH, further protecting the exposed 6-OH with acyl to obtain a fully protected thioglucoside compound, hydrolyzing the fully protected thioglucoside compound under a NBS or NIS condition to expose a terminal group OH, and reacting the terminal group —OH with CF$_3$CNPhCl to obtain a glucose building block A.

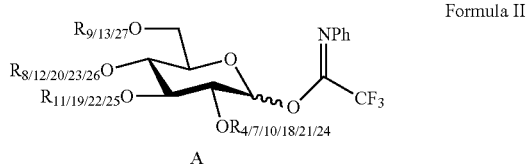

Formula II

A

Step 2, a galactose building block B is synthesized. The structure of the sugar building block B is as shown in the Formula III, the terminal group is protected by t-butyldibutylsilyl (TBS), and the remaining substituents R$_n$ are shown in the Formula I.

Specifically, the method for synthesizing the monosaccharide building block B comprises: using a compound 2,3-di-propylidene-6-benzylethylthiogalactose as a starting material, protecting 2-OH with Bz to obtain a 2-OBz compound, opening the propylidene group of the 2-OBz compound under the action of an acid to obtain a 2,3-dihydroxy compound, selectivity protecting 3-OH of the 2,3-dihydroxy compound with Bn to obtain a 3-OBn compound, protecting 4-OH of the 3-OBn compound with Lev to obtain a 4-Lev thioglycoside compound, hydrolyzing the 4-Lev thioglycoside compound by NBS to expose a anomeric group OH, reacting the anomeric group —OH with t-butyldimethylchlorosilane (TBSCl) to obtain a galactose with anomeric OH protected by TBS, and removing Lev with hydrazine acetate to obtain a galactose building block B.

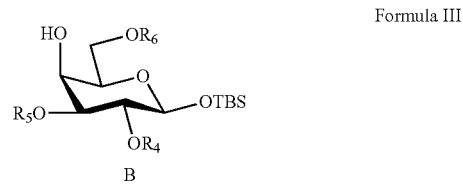

Formula III

B

Step 3, heptose building blocks C and D are synthesized. As shown in the Formula IV, the terminal group of the sugar building block C is protected by ethylthio group, and R$_{17}$ is protected by Nap; the terminal group of the sugar building block D is a linker, for example, O—(CH$_2$)$_n$—N(Bn)Cbz or O—(CH$_2$)$_n$—SBn or O—(CH$_2$)$_n$—N$_3$; R$_{17}$ is protected by acyl; and the remaining substituents R$_n$ are shown in Formula I.

Specifically, the method for synthesizing the monosaccharide building blocks C and D comprises: using 2,3-O-propylidene-4-O-benzylmannoethylthioside as a starting material, obtaining the corresponding aldehyde via Swern oxidation, after that, extending the carbon chain at 6-position via Wittig olefination to obtain a 6-deoxy olefin compound, dihydroxyating the olefin compound to obtain a 6,7-di-hydroxy compound, selectively protecting 7-OH by Nap using dibutyltin oxide (Bu$_2$SnO) to obtain a 7-Nap compound, protecting 6-OH with Bn to obtain a fully protected compound; removing the propylidene group of the fully protected compound under the condition of 80% acetic acid to obtain a 2,3-di-hydroxy compound, selectively protecting 3-OH with dibutyltin oxide (Bu$_2$SnO) and Nap to obtain the heptose building block C; protecting 2-OH of the building block C with Lev to obtain a 2-Lev compound, reacting the 2-Lev compound with a linker obtain a heptose compound with a terminal linker, removing 7-Nap under the action of DDQ to obtain a 7-OH compound, protecting the 7-OH compound with acetyl to obtain a 7-OAc compound, and finally removing Lev under the action of hydrazine acetate to obtain a heptose building block D.

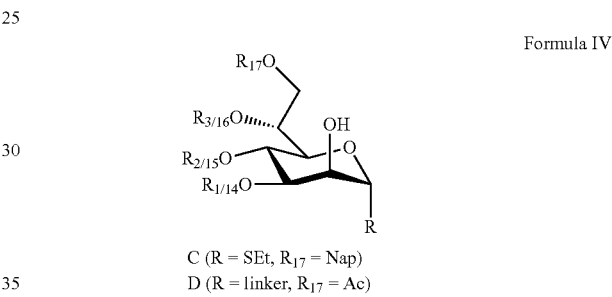

Formula IV

C (R = SEt, R$_{17}$ = Nap)
D (R = linker, R$_{17}$ = Ac)

Step 4, a trisaccharide donor is assembled. The trisaccharide building block G (Formula V) is synthesized using sugar building blocks. The condition for the glycosylation reaction is as follows. The reaction solvent is Et$_2$O/DCM, thiophene, being 10 equivalents of the donor is added, a 4 Å molecular sieve is used as a desiccant, the reaction temperature is 0° C., the reaction time is 3 to 5 h, and the reaction process is under argon gas protection. The reaction is monitored with a TLC plate. After completion of the reaction, the reaction is quenched with pyridine and the product is purified using a silica gel column. The terminal group of the trisaccharide G is N-phenyl-trifluoroacetimidate as a leaving group and the trisaccharide G serves as a glycosyl donor in the octasaccharide assembly.

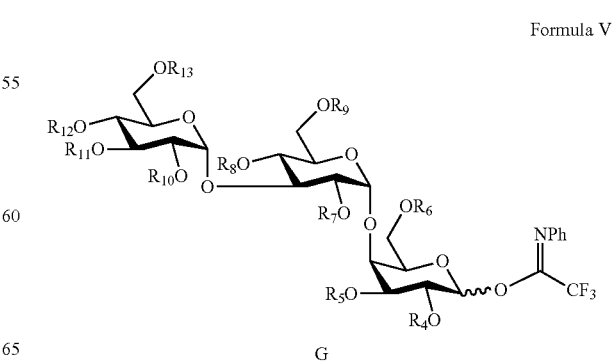

Formula V

G (substituents R$_n$ are shown in Formula I)

Step 5, a pentasaccharide acceptor is assembled. The pentasaccharide H (Formula VI) is synthesized using building block in hand, the glycosylation reaction condition for the glycoimidates is as follows. The reaction solvent is $Et_2O$/DCM, thiophene, being 10 equivalents of donor is added, a 4 Å molecular sieve is used as a desiccant, the reaction temperature is 0° C., the reaction time is 3 to 5 h, and the reaction process is under argon gas protection. The reaction is monitored with a TLC plate. After completion of the reaction, the reaction is quenched with pyridine and the product is purified using a silica gel column. In the glycosylation reaction process of thioglycoside, NIS/TMSOTf or NIS/TfOH is used as a promoter, DCM is used as a solvent and the 4 Å molecular sieve is used as a desiccant. The synthetic pentasaccharide serves as a glycosyl acceptor in the octasaccharide assembly.

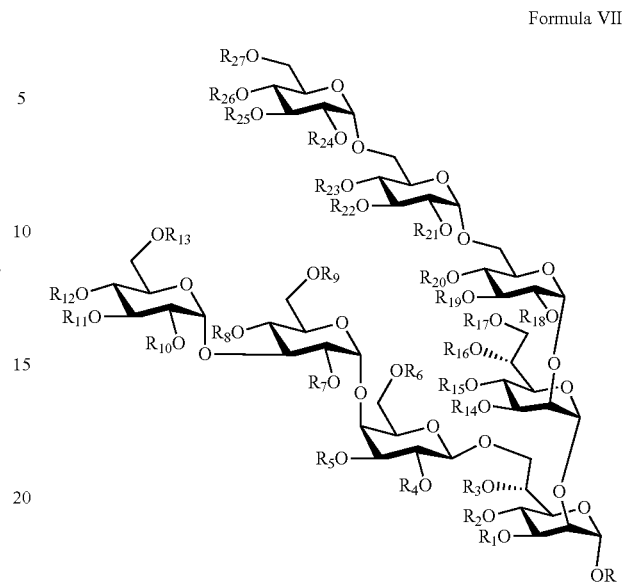

Formula VII

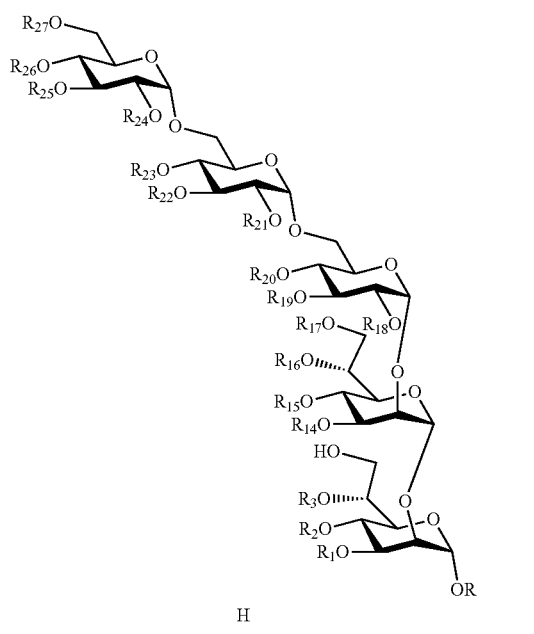

Formula VI

H (substituents $R_n$ are shown in Formula I)

Step 6, an octasaccharide is assembled, and the assembly of the octasaccharide adopts the [3+5] synthesis strategy. The reaction solvent is DCM, the promoter is TMSOTf, the reaction temperature is 0° C., the reaction time is 7 h, and the reaction process is under argon gas protection. The reaction is monitored with a TLC plate. After completion of the reaction, the reaction is quenched with pyridine and the product is purified using a silica gel column.

Step 7, the octasaccharide is deprotected. The acyl of the protected octasaccharide is removed under an alkaline condition. After purification by a silica gel column, the aromatic group is removed by using Pd/C, $H_2$ for 3 days. After the aromatic group is fully deprotected, the purification is carried out with a reverse phase C18 column to finally obtain the target octasaccharide as shown in Formula VIII.

Formula VIII

The disclosure also provides a method for generating a α-glycosidic bond of glucose, wherein the glycosyl donor and acceptor are co-distilled 2 to 3 times in toluene, dry DCM or DCM/$Et_2O$ is added; the substrate concentration is 0.01-0.1 M, the activated 3 Å or 4 Å molecular sieve is used as a desiccant, thiophene, being 8-10 equivalents of thiophene is added; the reaction is stirred at room temperature for 20-30 min, then cooled to −50-0° C., TMSOTf is added as a promotor, the reaction time is 1-7 h; and the reaction is terminated with pyridine.

Specifically, the glycosyl donor and acceptor are co-distilled three times in toluene, and dry DCM or DCM/Et$_2$O in a volume ratio of 1:2 is added; the substrate concentration is 0.02-0.05 M, the activated 3 Å or 4 Å molecular sieve is used as a desiccant, thiophene, being 10 equivalents of the glycosyl donor, is added; the reaction is stirred at room temperature for 20-30 min, then cooled to 0° C., TMSOTf is added as a promotor, the reaction time is 3-5 h; and the reaction is terminated with pyridine.

The beneficial effects of the disclosure are as follows.

The disclosure is the chemical synthesis of the outer core octasaccharide of *H. pylori*. In the present disclosure, a method which is very advantageous for the formation of α-glycosidic bond of glucose is found by a protecting group strategy, a solvent effect, and a temperature effect, and the method is applied to the synthesis of the outer core octasaccharide of *H. pylori*. The synthesized outer core octasaccharide of *H. pylori* is linked to an antigenic protein to form a glycoconjugate, which plays an important role in the development of a vaccine for the prevention and treatment of *H. pylori*.

DETAILED DESCRIPTION

The embodiments of the present disclosure will be described in detail below with reference to the embodiments. However, those skilled in the art will understand that the following embodiments are merely illustrative of the disclosure and are not intended to limit the scope of the disclosure. If no specific conditions are specified in the embodiments, they are carried out according to the general conditions or the conditions recommended by the manufacturer. Any reagents or instruments that are unspecified in the manufacturer are commercially available and conventional products.

The calculation method of the yield of the present disclosure is "product (mol)/reaction substrate (mol)*100%. The method for identifying the structure of the compound in the present disclosure is a nuclear magnetic resonance spectrum measurement (400 M/600 M/700 M), high resolution mass spectrometry measurement, and optical rotation measurement, and the results have been listed in the specific synthesis of each compound.

Embodiment 1

Figure 1:
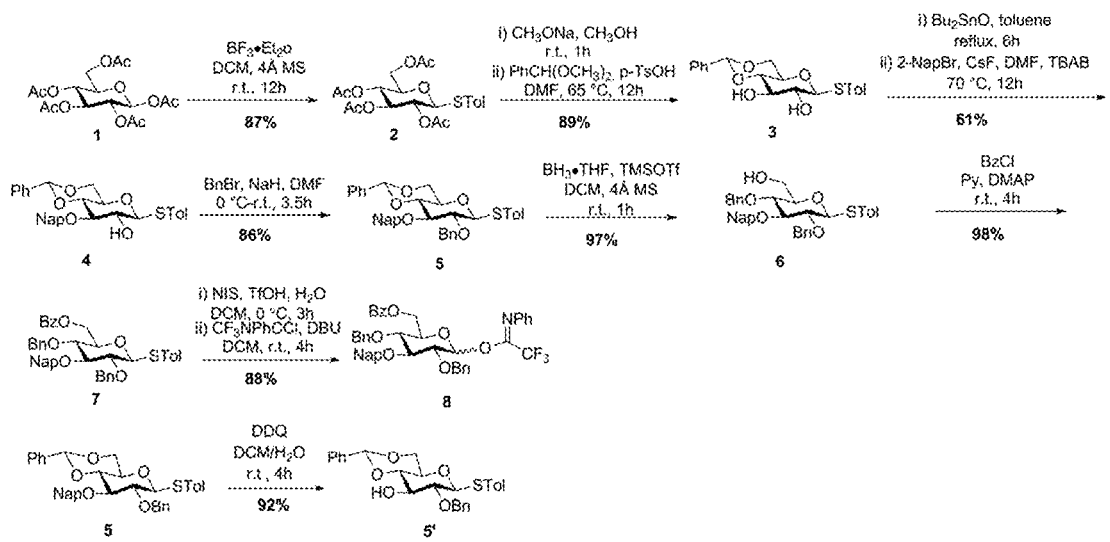
FIG. 1: Synthesis of sugar building block 8.

The synthesis of the building block 8 is shown in FIG. 1:

As shown in FIG. 1, peracetylated glucose 1 is used as a starting material and is reacted with p-thiocresol under the action of boron trifluoride etherate (BF$_3$.OEt$_2$) to form peracetylthioglycoside compound 2. The acetyl group is removed under the action of sodium methoxide (NaOCH$_3$) to expose four hydroxy groups. The tetrahydroxy compound and benzaldehyde dimethyl acetal (PhCH(OCH$_3$)$_2$) are reacted via the catalysis of p-toluenesulfonic acid (p-TsOH.H$_2$O) to form a 4,6-benzylidene protected thioglycoside compound 3. The 3-OH is selectively protected with 2-methylnaphthalene (2-Nap) to obtain a compound 4, and 2-OH is protected with benzyl (Bn) to obtain a compound 5. The 4,6-benzylidene group is selectively opened by using borane (BH$_3$.THF) and trimethylsilyl trifluoromethanesulfonate (TMSOTf) to expose 6-OH to obtain a compound 6. The 6-OH of compound 6 is protected with benzoyl (Bz) to obtain a fully protected thioglucoside compound 7. The thioglycoside is hydrolyzed under a NBS condition to expose a terminal group OH, and the terminal group —OH is reacted with CF$_3$CNPhCl to obtain a glucose building block 8.

Specific test operations and steps are as follows.

Compound 2:

Peracetyl glucose 1 (10.0 g, 25.6 mmol) was dissolved in DCM (128 mL). p-thiocresol (4.8 g, 38.6 mmol) and BF$_3$.OEt$_2$ (4.8 mL, 38.4 mmol) were added at 0° C. The reaction solution was warm up to room temperature and stirred for 12 h. The reaction solution was diluted with DCM and then washed with saturated NaHCO$_3$. The organic phase was dried with anhydrous Na$_2$SO$_4$, concentrated, then separated and purified by column chromatography (petroleum ether/ethyl acetate, 3:1) to obtain a compound 2 (10.1 g, 87%). [α]$^{22}_D$=11.6 (c 1.0, CH$_3$Cl); $^1$H NMR (400 MHz, Chloroform-d) δ=7.42-7.35 (m, 2H, Ar), 7.12 (m, J=7.8, 2H, Ar), 5.20 (dd, J=9.4, 9.4 Hz, 1H, H-3), 5.02 (dd, J=9.4, 9.8 Hz, 1H, H-4), 4.93 (dd, J=10.0, 9.4 Hz, 1H, H-2), 4.63 (d, J=10.0 Hz, 1H, H-1), 4.25-4.13 (m, 2H, H-6a, 6b), 3.70 (ddd, J=9.8, 4.8, 2.7 Hz, 1H, H-5), 2.35 (s, 3H, SPhCH$_3$), 2.09 (s, 3H, OAc), 2.08 (s, 3H, OAc), 2.01 (s, 3H, OAc), 1.98 (s, 3H, OAc). $^{13}$C NMR (101 MHz, CDCl$_3$) δ=170.6, 170.2, 169.4, 169.2, 138.8, 133.8, 129.7, 127.5, 85.8 (C-1), 75.8, 74.0, 69.9, 68.2, 62.1, 21.2, 20.8, 20.7, 20.6, 20.6; HRMS (ESI) m/z calcd for C$_{21}$H$_{26}$O$_9$SNa [M+Na]$^+$ 477.1190, found 477.1198.

Compound 3:

The compound 2 (7.3 g, 16.1 mmol) was dissolved in methanol (108 mL). MeONa (173 mg, 3.2 mmol) was added and the reaction was stirred at room temperature for 1 h. The reaction solution was neutralized with IR-120 resin (H$^+$), filtered and concentrated, and the crude product was boiled twice with toluene. The obtained crude product was dissolved in DMF (54 mL), and p-methylbenzaldehyde dimethyl acetal (3.6 mL, 24.1 mmol) and p-toluenesulfonic acid monohydrate (456 mg, 2.4 mmol) were added. The reaction was stirred at 65° C. for 12 h and quenched with NEt$_3$, concentrated and then purified by column chromatography (petroleum ether/ethyl acetate, 1:1) to obtain a compound 3 (5.4 g, 89%). [α]$^{22}_D$=25.6 (c 1.0, CH$_3$Cl). $^1$H NMR (400 MHz, Chloroform-d) δ=7.50-7.41 (m, 4H, Ar), 7.38-7.32 (m, 3H, Ar), 7.16-7.11 (m, 2H, Ar), 5.51 (s, 1H, ArCH), 4.54 (d, J=9.7 Hz, 1H, H-1), 4.36 (m, 1H, H-6a), 3.87-3.67 (m, 2H, H-6b, H-4), 3.52-3.44 (m, 2H, H-3, H-2), 3.41 (m, 1H, H-5), 2.93 (d, J=2.2 Hz, 1H, OH), 2.75 (d, J=2.4 Hz, 1H, OH), 2.36 (s, 3H, SPhCH$_3$); $^{13}$C NMR (101 MHz, CDCl$_3$) δ=138.9, 136.9, 133.7, 129.9, 129.3, 128.3, 127.2, 126.3, 101.9, 88.7 (C-1), 80.2, 74.5, 72.5, 70.5, 68.6, 21.2. HRMS (ESI) m/z calcd for C$_{20}$H$_{22}$O$_5$SNa [M+Na]$^+$ 397.1080, found 397.1078.

Compound 4:

The compound 3 (498 mg, 1.33 mmol) and Bu$_2$SnO (397 mg, 1.6 mmol) were dissolved in anhydrous toluene (4.3 mL) and heated to reflux for 6 h. The mixture was cooled to room temperature and concentrated. The crude product was dissolved in DMF (6.7 mL), and then CsF (260 mg, 1.73 mmol), TBAB (560 mg, 1.73 mmol), and 2-NapBr (350 mg, 1.6 mmol) were added. The reaction solution was stirred at 70° C. for 12 h. After the raw material was reacted completely, the mixture was concentrated under reduced pressure, dissolved in dichloromethane, sequentially washed with water and saturated brine, dried with anhydrous $MgSO_4$, concentrated and purified by column chromatography (petroleum ether/ethyl acetate, 5:1) to obtain a compound 4 (417 mg, 61%). $[\alpha]^{22}_D=-33.8$ (c 1.0, $CH_3Cl$). $^1H$ NMR (400 MHz, Chloroform-d) δ 7.89-7.59 (m, 4H, Ar), 7.51-7.41 (m, 7H, Ar), 7.39-7.34 (m, 3H, Ar), 7.12 (m, J=7.9 Hz, 2H, Ar), 5.57 (s, 1H, ArCH), 5.09 (d-like, J=11.8 Hz, 1H, ArCH), 4.96 (d-like, J=11.8 Hz, 1H, ArCH), 4.55 (d, J=9.7 Hz, 1H, H-1), 4.37 (dd, J=10.5, 4.9 Hz, 1H, H-6a), 3.78 (dd, J=10.5, 10.5 Hz, 1H, H-6b), 3.66 (m, 1H, H-4), 3.66 (dd, J=9.2, 9.2 Hz, 1H, H-3), 3.56-3.42 (m, 2H, H-2, H-5), 2.57 (s, 1H, OH), 2.34 (s, 3H, $SPhCH_3$). $^{13}C$ NMR (101 MHz, $CDCl_3$) δ=138.8, 137.2, 135.7, 133.8, 133.3, 133.1, 129.8, 129.0, 128.3, 128.2, 127.9, 127.7, 127.2, 126.9, 126.1, 126.0, 126.0, 125.9, 101.4, 88.7 (C-1), 81.5, 81.1, 74.8, 72.3, 70.8, 68.7. HRMS (ESI) m/z calcd for $C_{31}H_{30}O_5SNa$ $[M+Na]^+$ 537.1706, found 537.1701.

Compound 5:

The compound 4 (130 mg, 0.25 mmol) was dissolved in anhydrous DMF (1.4 mL), and the solution was cooled to 0° C. NaH (22.4 mg, 0.56 mmol) was added and then BnBr (49.9 uL, 0.42 mmol) was added. The reaction solution was stirred at room temperature for 3.5 h. After the reactant disappeared, the solution was cooled to 0° C., and water was added dropwise to quench the reaction. The reaction solution was extracted with DCM three times. The organic phase was dried with anhydrous $Na_2SO_4$, concentrated, separated and purified by column chromatography (petroleum ether/ethyl acetate, 6:1) to obtain a compound 5 (130 mg, 86%). $[\alpha]^{22}_D=-9.3$ (c 1.0, $CH_3Cl$). $^1H$ NMR (400 MHz, Chloroform-d) δ 7.86-7.62 (m, 4H, Ar), 7.52-7.27 (m, 15H, Ar), 7.11 (d, J=7.9 Hz, 2H, Ar), 5.60 (s, 1H, ArCH), 5.08 (d-like, J=11.4 Hz, 1H, ArCH), 4.93 (d-like, J=11.4 Hz, 1H, ArCH), 4.90 (d-like, J=10.4 Hz, 1H, ArCH), 4.83 (d-like, J=10.4 Hz, 1H, ArCH), 4.70 (d, J=9.8 Hz, 1H, H-1), 4.38 (dd, J=10.3, 5.0 Hz, 1H, H-6a), 3.88 (dd, J=9.4, 8.3 Hz, 1H, H-3), 3.80 (dd, J=10.3, 9.8 Hz, 1H, H-6b), 3.71 (dd, J=9.4, 9.4 Hz, 1H, H-4), 3.51 (dd, J=9.8, 8.3 Hz, 1H, H-2), 3.45 (ddd, J=9.7, 9.8, 4.9 Hz, 1H, H-5), 2.33 (s, 3H, $SPhCH_3$); $^{13}C$ NMR (101 MHz, $CDCl_3$) δ 138.2, 138.1, 137.3, 135.8, 133.3, 133.0, 133.0, 129.8, 129.2, 129.0, 128.4, 128.3, 128.2, 128.1, 127.9, 127.8, 127.6, 126.8, 126.2, 126.0, 126.0, 125.8, 101.2, 88.6 (C-1), 83.0, 81.5, 80.5, 75.8, 75.3, 70.2, 68.7, 21.1. HRMS (ESI) m/z calcd for $C_{38}H_{36}O_5SNa$ $[M+Na]^+$ 627.2176, found 627.2171.

Compound 5':

The compound 5 (768 mg, 1.1 mmol) was dissolved in a mixed solvent of $DCM/H_2O$ (9:1, v/v, 48.9 mL), and the reaction solution was cooled to 0° C. 2,3-dichloro-5,6-dicyano-1,4-benzoquinone (DDQ) (186 mg, 0.82 mmol) was added. The reaction temperature was raised to room temperature and the reaction was continued for 4 h. The reaction solution was diluted with DCM, sequentially washed with 10% of $Na_2S_2O_3$ solution and saturated $NaHCO_3$ solution, dried with $Na_2SO_4$, filtered, concentrated, separated and purified by column chromatography (petroleum ether/ethyl acetate, 10:1) to obtain a compound 5' (275 mg, 92%). Structural identification data has been reported in the literature.

Compound 6:

Compound 5 (455 mg, 0.75 mmol) was dissolved in dry DCM (3.75 mL). The solution was cooled to 0° C., and $BH_3.THF$ (1 M, 3.75 mL) was added and was stirred at 0° C. for 10 min, and TMSOTf (20.3 μL, 0.11 mmol) was added dropwise. The reaction solution was returned to room temperature and stirred for 1 h. After the raw material disappeared, the reaction was terminated by the addition of saturated $NaHCO_3$. The mixture was extracted with DCM three times, dried with anhydrous $Na_2SO_4$, concentrated, filtered, separated and purified by column chromatography (petroleum ether/ethyl acetate, 5:1) to obtain a compound 6 (441 mg, 97%). $[\alpha]^{22}_D=17.1$ (c 1.0, $CH_3Cl$). $^1H$ NMR (400 MHz, Chloroform-d) δ 7.86-7.62 (m, 4H, Ar), 7.51-7.35 (m, 6H, Ar), 7.36-7.24 (m, 8H, Ar), 7.12 (d, J=7.9 Hz, 2H, Ar), 5.06 (d-like, J=11.2 Hz, 1H, ArCH), 5.01 (d-like, J=11.2 Hz, 1H, ArCH), 4.95 (d-like, J=10.3 Hz, 1H, ArCH), 4.87 (d-like, J=11.0 Hz, 1H, ArCH), 4.78 (d-like, J=10.3 Hz, 1H, ArCH), 4.67 (d-like, 1H, 11.0 Hz, ArCH), 4.66 (d, J=9.8 Hz, 1H, H-1), 3.88 (ddd, J=12.0, 6.3, 2.7 Hz, 1H, H-6a), 3.77 (dd, J=9.1, 8.9 Hz, 1H, H-3), 3.70 (ddd, J=12.0, 7.3, 4.9 Hz, 1H, H-6b), 3.59 (dd, J=9.1, 9.5 Hz, 1H, H-4), 3.49 (dd, J=9.8, 8.9 Hz, 1H, H-2), 3.38 (ddd, J=9.5, 4.9, 2.7 Hz, 1H, H-5), 2.34 (s, 3H, $SPhCH_3$), 1.91 (dd, J=6.3, 7.3 Hz, 1H, OH). $^{13}C$ NMR (101 MHz, $CDCl_3$) δ 138.1, 138.0, 137.9, 135.8, 133.3, 133.0, 132.7, 129.8, 129.5, 128.5, 128.4, 128.2, 128.0, 127.9, 127.9, 127.9, 127.7, 126.5, 126.1, 125.9, 125.8, 87.8 (C-1), 86.6, 81.2, 79.3, 77.7, 75.8, 75.5, 75.1, 62.2, 21.1. HRMS (ESI) m/z calcd for $C_{38}H_{38}O_5SNa$ $[M+Na]^+$ 629.2332, found 629.2324.

Compound 7:

The compound 6 (194 mg, 0.33 mmol) was dissolved in pyridine (3.2 mL) and stirred at 0° C. for 5 min. BzCl (74 μL, 0.64 mmol) and a catalytic amount of DMAP were added. The reaction solution was stirred at room temperature for 4 h. The reaction solution was sequentially washed with saturated $NaHCO_3$ and brine, dried with anhydrous $Na_2SO_4$, concentrated and purified by column chromatography (petroleum ether/ethyl acetate, 5:1) to obtain a compound 7 (224 mg, 98%). $[\alpha]^{22}_D=9.1$ (c 1.0, $CH_3Cl$). $^1H$ NMR (400 MHz, Chloroform-d) δ 8.13-7.85 (m, 2H, Ar), 7.87-7.65 (m, 4H, Ar), 7.65-7.50 (m, 1H, Ar), 7.52-7.38 (m, 9H, Ar), 7.37-7.29 (m, 3H, Ar), 7.28-7.17 (m, 5H, Ar), 7.04-6.66 (m, 2H, Ar), 5.08 (d-like, J=11.0 Hz, 1H, ArCH), 5.01 (d-like, J=11.0 Hz, 1H, ArCH), 4.97 (d-like, J=10.3 Hz, 1H, ArCH), 4.90 (d-like, J=10.8 Hz, 1H, ArCH), 4.77 (d-like, J=10.3 Hz, 1H, ArCH), 4.68 (dd, J=11.9, 1.6 Hz, 1H, H-6a), 4.64 (d-like, J=10.8 Hz, 1H, ArCH), 4.64 (d, J=9.7 Hz, 1H, H-1), 4.46 (dd, J=11.9, 4.5 Hz, 1H, H-6b), 3.81 (dd, J=8.8, 8.8 Hz, 1H, H-3), 3.70-3.63 (m, 2H, H-4, H-5), 3.52 (dd, J=9.7, 8.8 Hz, 1H, H-2), 2.26 (s, 3H, $SPhCH_3$); $^{13}C$ NMR (101 MHz, $CDCl_3$) δ 166.1, 138.1, 137.9, 137.6, 135.7, 133.3, 133.1, 133.1, 133.0, 130.0, 129.8, 129.6, 129.2, 128.5, 128.5, 128.4, 128.3, 128.2, 128.1, 128.0, 127.9, 127.9, 127.7, 126.7, 126.1, 126.0, 125.9, 87.5 (C-1), 86.8, 80.8, 77.7, 76.1, 75.5, 75.3, 75.2, 63.6, 21.1. HRMS (ESI) m/z calcd for $C_{45}H_{42}O_6SNa$ $[M+Na]^+$ 733.2594, found 733.2589.

Compound 8:

The compound 7 (100 mg, 0.14 mmol) was dissolved in $DCM/H_2O$ (v/v, 10:1, 7 mL). The solution was cooled to 0° C. and TfOH (1.2 uL, 0.014 mmol) was added. The reaction was stirred at 0° C. for 3 h and terminated by the addition of $NEt_3$. The reaction solution was washed with saturated $NaHCO_3$, dried with anhydrous $Na_2SO_4$, concentrated and purified by column chromatography to obtain an intermediate (78.6 mg). The intermediate was dissolved in dry DCM (3.75 ml). The reaction solution was cooled to 0° C. and N-phenyltrifluoroacetyl chloride (97 μl, 0.365 mmol) and DBU (58 μl, 0.39 mmol) were added. The reaction was stirred at room temperature for 2 h. The reaction solution was concentrated and purified by column chromatography (petroleum ether/ethyl acetate, 20:1) to obtain a compound 8 (96 mg, 88%). $[\alpha]^{22}_D=71.3$ (c 1.0, $CH_3Cl$). $^1H$ NMR (400 MHz, Chloroform-d) δ 8.14-8.00 (m, 5H), 7.94-7.73 (m, 12H), 7.68-7.07 (m, 37H), 6.87-6.67 (m, 5H), 6.55 (bs, 1H, H-1α), 5.80 (bs, 1H, H-1β), 5.27-4.80 (m, 13H, ArCH), 4.75-4.55 (m, 8H, ArCH, H-6α, H-6β), 4.26-4.12 (m, 2H), 3.94-3.63 (m, 8H). $^{13}$C NMR (101 MHz, CDCl$_3$) δ 166.2, 166.1, 143.5, 143.4, 137.7, 137.6, 137.5, 137.4, 135.8, 135.6, 133.4, 133.3, 133.2, 133.2, 133.1, 129.8, 129.7, 129.1, 128.8, 128.7, 128.6, 128.6, 128.6, 128.5, 128.4, 128.3, 128.3, 128.3, 128.2, 128.2, 128.1, 128.1, 128.0, 128.0, 128.0, 127.8, 127.7, 127.7, 126.9, 126.7, 126.2, 126.2, 126.1, 126.1, 126.0, 126.0, 125.9, 125.3, 124.4, 124.2, 119.4, 119.3, 97.0 (C-1β), 93.0 (C-1α), 84.5, 81.6, 80.8, 79.5, 77.3, 76.1, 75.9, 75.5, 75.5, 75.3, 75.2, 73.9, 73.4, 71.7, 63.2, 63.0, 21.5. HRMS (ESI) m/z calcd for C$_{46}$H$_{40}$F$_3$NO$_7$Na [M+Na]$^+$ 798.2649.

Embodiment 2

Figure 2:
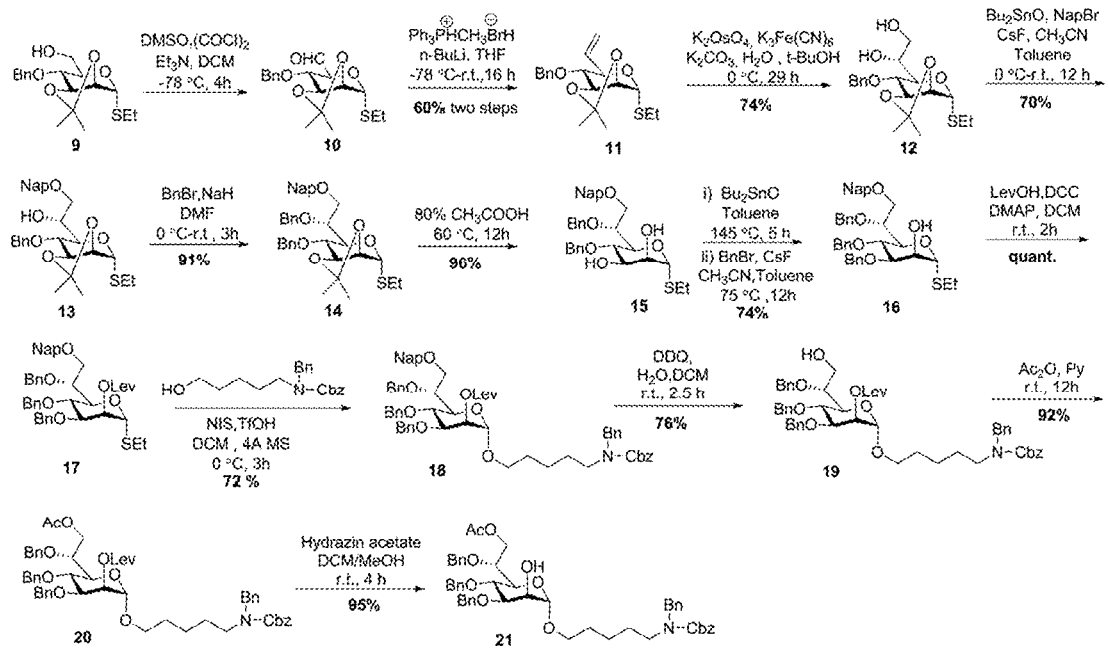
FIG. 2: Synthesis of sugar building block 21.

The synthesis route of the building block 21 is shown in FIG. 2.

As shown in FIG. 2, 2,3-O-propylidene-4-O-benzylmannoethylthioside 9 is used as a starting material, and subjected to Swern oxidation to obtain a corresponding aldehyde compound 10. Then, the carbon chain at 6-position is extended by witting to obtain a 6-deoxy olefin compound 11. The olefin compound is subjected to dihydroxylation under the co-action of potassium osmate (K$_2$OsO$_4$), potassium ferricyanate (K$_3$Fe(CN)$_6$) and potassium carbonate (K$_2$CO$_3$) to obtain a 6,7-di-hydroxy compound 12. 7-OH of a compound 13 is selectively protected with Nap by using dibutyltin oxide (Bu$_2$SnO), and 6-OH is protected with Bn to obtain a compound 14. A compound 15 is obtained after removal of the propylidene group under the action of 80% acetic acid, and 3-OH was selectively protected with Nap to obtain a heptose building block 16. 2-OH of the sugar building block 16 is protected with Lev to obtain a compound 17. The compound 17 is reacted with a five carbon linker to obtain a heptose 18 with the terminal group linker. 7-Nap is removed under the action of DDQ to obtain a compound 19. 7-OH of the compound is protected with acetyl to obtain a compound 20, and finally, Lev is removed under the action of hydrazine acetate to obtain a heptose building block 21.

Specific test operations and steps are as follows.

Compound 11:

Oxalyl chloride (0.36 mL, 4.23 mmol) was dissolved in dry DCM (2.2 mL), and the temperature of the solution was lowered to −78° C. DMSO (0.6 mL, 8.46 mmol) dissolved in DCM (3 mL) was added dropwise to the oxalyl chloride solution, and the reaction was stirred at −78° C. for 0.5 h. A compound 9 (1.0 g, 2.82 mmol) was dissolved in DCM (11.5 mL) and added dropwise to the reaction solution. The reaction solution was stirred at −78° C. for 1 h, NEt$_3$ was added, and the reaction temperature was gradually returned to room temperature within 4 h. After the reaction of the raw material was completed, water was added to terminate the reaction. The reaction solution was extracted with DCM. The organic phase was sequentially washed with water and saturated brine, dried with anhydrous Na$_2$SO$_4$, and concentrated. The methyltriphenyl phosphonium bromide was dissolved in THF, and the solution was stirred at 0° C. n-BuLi (4.7 mL, 11.3 mmol, 2.4 M in THF) was added to a reaction flask, and the reaction temperature was lowered to −78° C. after stirring for 30 min. The crude product of the previous step was dissolved in THF (5 mL), and was added dropwise to the reaction solution. The reaction was gradually returned to room temperature and the reaction was continued for 12 h. The reaction was terminated by the addition of saturated NH$_4$Cl. The reaction solution was extracted with ethyl acetate three times, dried with anhydrous Na$_2$SO$_4$, concentrated and purified by column chromatography (petroleum ether/ethyl acetate, 20:1) to obtain a compound 11 (592 mg, 60%). [α]$^{22}_D$=129.25 (c 1.0, CH$_3$Cl). $^1$H NMR (400 MHz, Chloroform-d) δ 7.39-7.26 (m, 5H, Ar), 5.99 (ddd, J=17.3, 10.6, 5.5 Hz, 1H, H-6), 5.58 (s, 1H, H-1), 5.41 (ddd, J=17.3, 1.6, 1.6 Hz, 1H, H-7a), 5.25 (ddd, J=10.6, 1.6, 1.6 Hz, 1H, H-7b), 4.85 (d-like, J=11.6 Hz, 1H, ArCH), 4.63 (d-like, J=11.6 Hz, 1H, ArCH), 4.42 (dddd, J=10.0, 5.5, 1.6, 1.6 Hz, 1H, H-5), 4.29 (dd, J=7.2, 5.7 Hz, 1H, H-3), 4.19 (d, J=5.7 Hz, 1H, H-2), 3.38 (dd, J=10.0, 7.2 Hz, 1H, H-4), 2.72-2.39 (m, 2H, SCH$_2$CH$_3$), 1.49 (s, 3H, CH$_3$), 1.36 (s, 3H, CH$_3$), 1.28 (t, J=7.4 Hz, 3H, SCH$_2$CH$_3$); $^{13}$C NMR (101 MHz, CDCl$_3$) δ 138.2, 134.9, 128.2, 128.0, 127.6, 117.3, 109.4, 80.1 (C-1), 79.5, 78.5, 73.2, 69.5, 28.0, 26.4, 24.4, 14.6. HRMS (ESI) m/z calcd for C$_{19}$H$_{26}$O$_4$SNa [M+Na]$^+$ 373.1449, found 373.1447.

Compound 12:

K$_2$OsO$_2$(OH)$_4$ (103 mg, 0.28 mmol), K$_3$Fe(CN)$_6$ (11.2 g, 33.9 mmol) and K$_2$CO$_3$ (5.2 g, 37.3 mmol) were added to tert-butanol (56.5 mL) and water (56.5 mL) in a reaction flask. The reaction solution was cooled to 0° C., and the compound 11 was dissolved in toluene (22 mL), and was added to the reaction flask. The reaction was stirred at 0° C. for 29 h. After the raw material disappeared completely, and the reaction was extracted with ethyl acetate. The organic phase was washed with 1 M KOH, dried with anhydrous Na$_2$SO$_4$, filtered, concentrated, separated and purified by column chromatography (petroleum ether/ethyl acetate, 1:1) to obtain a compound 12 (3.2 g, 74%). [α]$^{22}_D$=173.6 (c 1.0, CH$_3$Cl). $^1$H NMR (400 MHz, Chloroform-d) δ 7.43-7.28 (m, 5H, Ar), 5.55 (s, 1H, H-1), 4.98 (d-like, J=11.4 Hz, 1H, ArCH), 4.64 (d-like, J=11.4 Hz, 1H, ArCH), 4.32 (dd, J=7.0, 5.7 Hz, 1H, H-3), 4.20 (d, J=5.7 Hz, 1H, H-2), 4.06 (dd, J=9.9, 6.3 Hz, 1H, H-5), 3.88 (dt, J=6.3, 4.2 Hz, 1H, H-6), 3.69 (dd, J=9.9, 7.0 Hz, 1H, H-4), 3.65 (m, 2H, H-7a, H-7b), 3.54 (bs, 1H, OH), 2.80-2.47 (m, 2H, SCH$_2$CH$_3$), 2.27 (bs, 1H, OH), 1.54 (s, 3H, CH$_3$), 1.37 (s, 3H, CH$_3$), 1.29 (t, J=7.4 Hz, 3H, SCH$_2$CH$_3$); $^{13}$C NMR (101 MHz, CDCl$_3$) δ 137.2, 128.6, 128.3, 128.2, 109.6, 79.6 (C-1), 79.5, 78.3, 76.5, 73.2, 72.8, 67.7, 62.8, 28.1, 26.3, 24.1, 14.1. HRMS (ESI) m/z calcd for C$_{19}$H$_{28}$O$_6$SNa [M+Na]$^+$ 407.1499, 407.1491.

Compound 13:

The compound 12 (11.2 mg, 29.3 mmol) was dissolved in toluene (146 mL). Bu$_2$SnO (10.9 g, 44 mmol) was added to a reaction flask, and the reaction solution was heated to reflux for 4 h. Half of the toluene was distilled off and the reaction solution was cooled to room temperature. CsF (6.7 g, 44 mmol), 2-NapBr (9.7 g, 44 mmol), and CH$_3$CN (73.3 mL) were added. The reaction solution was reacted at 70° C. overnight. The reaction solution was filtered through diatomite, concentrated, separated and purified by column chromatography (petroleum ether/ethyl acetate, 3:1) to obtain a compound 13 (3.2 g, 74%). [α]$^{22}_D$=78.4 (c 1.0, CH$_3$Cl). $^1$H NMR (400 MHz, Chloroform-d) δ 7.83-7.75 (m, 4H, Ar), 7.47-7.33 (m, 3H, Ar), 7.33-7.26 (m, 5H, Ar), 5.51 (s, 1H, H-1), 4.91 (d-like, J=11.4 Hz, 1H, ArCH), 4.70 (d-like, J=12.0 Hz, 1H, ArCH), 4.65 (d-like, J=12.0 Hz, 1H, ArCH), 4.59 (d-like, J=11.3 Hz, 1H, ArCH), 4.30 (dd, J=6.6, 5.8 Hz, 1H, H-3), 4.17 (dd, J=5.8, 1H, H-2), 4.12 (m, 1H, H-6), 4.09 (dd, J=9.6, 4.8 Hz, 1H, H-5), 3.70 (dd, J=9.6, 6.6 Hz, 1H, H-4), 3.61 (m, 2H, H-7a, H-7b), 3.02 (d, J=2.9 Hz, 1H, OH), 2.70-2.37 (m, 2H, SCH$_2$CH$_3$), 1.51 (s, 3H, CH$_3$), 1.36 (s, 3H, CH$_3$), 1.21 (t, J=7.4 Hz, 3H, SCH$_2$CH$_3$); $^{13}$C NMR (101 MHz, CDCl$_3$) δ 137.7, 135.7, 133.3, 133.0, 128.4, 128.4, 128.1, 128.1, 127.9, 127.8, 127.7, 126.4, 126.0, 125.8, 125.7, 109.5, 79.7 (C-1), 78.6, 78.0, 76.7, 76.5, 73.6, 72.8, 72.3, 71.0, 68.5, 28.0, 26.4, 24.1, 14.2. HRMS (ESI) m/z calcd for $C_{30}H_{36}O_6SNa$ [M+Na]$^+$ 547.2125, found 547.2135.

Compound 14:

The compound 13 (10.3 g, 19.6 mmol) was dissolved in anhydrous DMF (1.4 mL), and the solution was cooled to 0° C. NaH (1.56 g, 39.2 mmol) was added and then BnBr (4.7 mL, 39.2 mmol) was added. The reaction solution was stirred at room temperature for 3.5 h. After the reactant disappeared, the solution was cooled to 0° C., and water was added dropwise to quench the reaction. The reaction solution was extracted with DCM three times. The organic phase was dried with anhydrous $Na_2SO_4$, concentrated, separated and purified by column chromatography (petroleum ether/ethyl acetate, 10:1) to obtain a compound 14 (11.0 g, 91%). $^1$H NMR (400 MHz, Chloroform-d) δ 7.83-7.69 (m, 4H, Ar), 7.49-7.24 (m, 13H, Ar), 5.55 (s, 1H, H-1), 4.82 (d-like, J=11.4 Hz, 1H, ArCH), 4.74 (d-like, J=11.8 Hz, 1H, ArCH), 4.69 (d-like, J=11.8 Hz, 1H, ArCH), 4.65 (d-like, J=12.3 Hz, 1H, ArCH), 4.59 (d-like, J=12.3 Hz, 1H, ArCH), 4.53 (d-like, J=11.4 Hz, 1H, ArCH), 4.33-4.23 (m, 2H, H-3, H-5), 4.14 (d, J=5.6 Hz, 1H, H-2), 4.08 (ddd, J=5.8, 5.3, 1.5 Hz, 1H), 3.75-3.72 (m, 2H, H-7a, H-7b), 3.70 (dd, J=10.3, 6.9 Hz, 1H, H-4), 2.77-2.41 (m, 2H, $SCH_2CH_3$), 1.41 (s, 3H, $CH_3$), 1.34 (s, 3H, $CH_3$), 1.22 (t, J=7.4 Hz, 3H, $SCH_2CH_3$); $^{13}$C NMR (101 MHz, CDCl$_3$) δ 138.7, 138.2, 136.0, 133.3, 132.9, 128.2, 128.2, 128.0, 127.9, 127.8, 127.7, 127.6, 127.5, 127.4, 126.2, 126.0, 125.7, 125.6, 109.3, 79.5 (C-1), 79.0, 77.8, 76.4, 76.3, 73.2, 72.7, 72.5, 70.5, 69.3, 28.0, 26.5, 23.8, 14.3. HRMS (ESI) m/z calcd for $C_{37}H_{42}O_6SNa$ [M+Na]$^+$ 637.2594, found 637.2587.

Compound 15:

The compound 14 was dissolved in 80% aqueous acetic acid, and the reaction solution was stirred at 60° C. for 12 h. The TLC plate showed the complete reaction of the raw material. After concentration, the reaction solution was diluted with DCM, washed with saturated NaHCO$_3$, dried with Na$_2$SO$_4$, filtered, concentrated, separated and purified by column chromatography (petroleum ether/ethyl acetate, 3:1) to obtain a compound 15 (9.8 g, 96%). [α]$^{22}_D$=71.5 (c 1.0, CH$_3$Cl). $^1$H NMR (400 MHz, Chloroform-d) δ 7.92-7.70 (m, 4H, Ar), 7.50-7.27 (m, 8H, Ar), 7.25-7.15 (m, 5H, Ar), 5.26 (d, J=1.9 Hz, 1H, H-1), 4.76 (d-like, J=11.9 Hz, 1H, ArCH), 4.71 (d-like, J=11.9 Hz, 1H, ArCH), 4.70-4.61 (m, 4H, ArCH), 4.30 (dd, J=9.4, 1.6 Hz, 1H, H-5), 4.03 (ddd, J=6.8, 5.2, 1.6 Hz, 1H, H-6), 3.94 (dd, J=3.4, 1.9 Hz, 1H, H-2), 3.89 (dd, J=8.6, 3.3 Hz, 1H, H-3), 3.84 (dd, J=10.2, 5.2 Hz, 1H, H-7a), 3.84 (dd, J=9.4, 8.6 Hz, 1H, H-4), 3.74 (dd, J=10.2, 6.8 Hz, 1H, H-7b), 2.75-2.49 (m, 2H, $SCH_2CH_3$), 2.45 (bs, 1H, OH), 2.23 (bs, 1H, OH), 1.24 (t, J=7.4 Hz, 3H, $SCH_2CH_3$); $^{13}$C NMR (101 MHz, CDCl$_3$) δ 138.7, 138.3, 135.8, 133.4, 133.1, 128.7, 128.4, 128.3, 128.1, 128.0, 127.9, 127.8, 127.7, 126.6, 126.2, 126.0, 125.9, 83.5 (C-1), 77.8, 76.5, 74.4, 73.6, 72.7, 72.6, 72.2, 71.7, 70.6, 24.8, 14.9. HRMS (ESI) m/z calcd for $C_{34}H_{38}O_6SNa$ [M+Na]$^+$ 597.2281, found 597.2278.

Compound 16:

The compound 15 (50 mg, 87 umol) was dissolved in toluene (0.58 mL), and Bu$_2$SnO (24.9 mg, 0.1 mmol) was added to a reaction flask. The reaction solution was heated to reflux for 3 h and cooled to room temperature. CsF (15.2 mg, 0.1 mmol), TBAB (32.2 mg, 0.1 mmol), and BnBr (11.9 µL, 4 mmol) were added. The reaction solution was heated for reflux for 3 h. The reaction solution was filtered through diatomite, concentrated, separated and purified by column chromatography (petroleum ether/ethyl acetate, 3:1) to obtain a compound 16 (43 mg, 74%). [α]$^{22}_D$=87.2 (c 1.0, CH$_3$Cl). $^1$H NMR (400 MHz, Chloroform-d) δ 7.85-7.67 (m, 4H), 7.49-7.35 (m, 5H), 7.34-7.07 (m, 13H), 5.34 (d, J=1.5 Hz, 1H, H-1), 4.96-4.53 (m, 8H, ArCH), 4.32 (dd, J=9.7, 1.3 Hz, 1H, H-5), 4.06 (dd, J=3.4, 1.8 Hz, 1H, H-2), 4.04-4.01 (m, 1H, H-6), 3.92 (dd, J=9.7, 9.1 Hz, 1H, H-4), 3.85 (dd, J=9.1, 3.2 Hz, 1H, H-3), 3.80 (dd, J=10.3, 4.7 Hz, 1H, H-7a), 3.74 (dd, J=10.3, 6.9 Hz, 1H, 7H-b), 2.77-2.26 (m, 3H, $SCH_2CH_3$, OH), 1.24 (t, J=7.4 Hz, 3H, $SCH_2CH_3$); $^{13}$C NMR (101 MHz, CDCl$_3$) δ 138.7, 138.7, 138.3, 138.2, 137.5, 137.5, 135.9, 135.9, 133.3, 132.9, 128.6, 128.6, 128.3, 128.3, 128.2, 128.2, 128.1, 128.0, 128.0, 128.0, 127.9, 127.8, 127.8, 127.7, 127.6, 127.6, 127.5, 127.4, 127.4, 126.2, 126.0, 126.0, 125.7, 125.7, 83.0 (C-1), 80.9, 78.0, 74.7, 74.6, 73.3, 72.3, 72.1, 71.8, 70.8, 69.6, 69.6, 24.6, 14.7. HRMS (ESI) m/z calcd for $C_{41}H_{44}O_6SNa$ [M+Na]$^+$ 687.2751, found 687.2753.

Compound 17:

The compound 16 (728 mg, 1.1 mmol) was dissolved in DCM (24 mL). LevOH (192 mg, 1.65 mmol), dicyclohexylcarbodiimide (DCC) (340 mg, 1.65 mmol), and N,N-dimethylpyridine (DMAP) (202 mg, 1.65 mmol) were added. The reaction was stirred at room temperature for 2 h, concentrated, separated and purified by column chromatography (petroleum ether/ethyl acetate, 3:1) to obtain a compound 17 (839 mg, 100%). [α]$^{22}_D$=54.8 (c 1.0, CH$_3$Cl). $^1$H NMR (400 MHz, Chloroform-d) δ 7.85-7.71 (m, 4H, Ar), 7.50-7.36 (m, 5H, Ar), 7.35-7.22 (m, 11H, Ar), 7.15 (m, 2H, Ar), 5.40 (dd, J=2.9, 1.7 Hz, 1H, H-2), 5.25 (d, J=1.7 Hz, 1H, H-1), 4.85-4.57 (m, 8H, ArCH), 4.31 (d, J=9.1 Hz, 1H, H-5), 4.04 (ddd, J=6.9, 4.6, 1.2 Hz, 1H, H-6), 3.95 (dd, J=9.1, 9.1 Hz, 1H, H-4), 3.91 (dd, J=9.1, 2.8 Hz, 1H, H-3), 3.79 (dd, J=10.4, 4.6 Hz, 1H, H-7a), 3.73 (dd, J=10.4, 6.9 Hz, 1H, H-7b), 2.82-2.35 (m, 6H, $SCH_2CH_3$, $C(O)CH_2CH_2(O)C$), 2.09 (s, 3H, $CH_3$), 1.24 (t, J=7.4 Hz, 3H, $SCH_2CH_3$); $^{13}$C NMR (101 MHz, CDCl$_3$) δ 206.2, 171.9, 138.7, 138.3, 137.6, 135.9, 133.2, 132.9, 128.4, 128.3, 128.3, 128.2, 128.2, 128.1, 128.0, 127.9, 127.8, 127.8, 127.8, 127.6, 127.5, 127.5, 127.4, 126.2, 126.1, 126.0, 125.7, 125.6, 82.0 (C-1), 78.9, 78.4, 76.7, 74.8, 74.5, 73.3, 72.3, 72.2, 71.6, 71.0, 70.4, 37.9, 29.7, 28.0, 25.3, 14.8. HRMS (ESI) m/z calcd for $C_{46}H_{50}O_8SNa$ [M+Na]$^+$ 785.3119, found 785.3106.

Compound 18:

The compound 17 (595 mg, 0.78 mmol) and N-benzyl-N-benzyloxycarbonyl-5-amino-pentanol (510 mg, 0.78 mmol) were co-distilled three times with toluene. Dry DCM (5 mL) and a 4 Å molecular sieve were added to the mixture. The mixture was stirred at room temperature for half an hour and then cooled to 0° C. NIS (211 mg, 0.94 mmol) and TMSOTf (14 µL, 78 ummol) were added and the reaction solution was stirred at 0° C. for 3 h. The reaction was terminated by the addition of NEt$_3$. After filtration, the solution was washed with 10% Na$_2$S$_2$O$_3$ solution and saturated NaHCO$_3$ solution, dried with Na$_2$SO$_4$, filtered, concentrated, separated and purified by column chromatography (petroleum ether/ethyl acetate, 2:1) to obtain a compound 18 (562 mg, 72%). [α]$^{22}_D$=11.5 (c 1.0, CH$_3$Cl). $^1$H NMR (400 MHz, Chloroform-d) δ 7.90-7.62 (m, 4H, Ar), 7.53-7.29 (m, 21H, Ar), 7.28-7.11 (m, 7H, Ar), 5.34 (d, J=3.1 Hz, 1H, H-2), 5.20 (d, J=11.0 Hz, 2H, COOCH$_2$Ph), 4.87 (d-like, J=10.6 Hz, 1H, ArCH), 4.83-4.74 (m, 3H, H-1, ArCH), 4.72-4.60 (m, 7H, ArCH), 4.08 (dd, J=6.7, 4.6 Hz, 1H, H-5), 3.99-3.90 (m, 3H, H-3, H-4, H-6), 3.83 (dd, J=10.4, 4.6 Hz, 1H, H-7a), 3.78 (dd, J=10.4, 6.7 Hz, 1H, H-7b), 3.63 (m, 1H, OCH$_2$), 3.37-3.16 (m, 3H, OCH$_2$, NCH$_2$), 2.75-2.51 (m, 4H, $C(O)CH_2CH_2(O)C$), 2.11 (s, 1H, $CH_3$), 1.66-1.45 (m, 4H, CH$_2$CH$_2$), 1.31-1.11 (m, 2H, CH$_2$); $^{13}$C NMR (101 MHz, CDCl$_3$) δ 206.3, 172.0, 138.8, 138.3, 138.0, 135.9, 133.3, 132.9, 128.6, 128.5, 128.4, 128.4, 128.3, 128.3, 128.1, 128.1, 128.0, 127.9, 127.9, 127.8, 127.7, 127.6, 127.6, 127.4, 127.2, 126.2, 126.1, 125.8, 125.6, 97.4 (C-1), 78.7, 78.3, 75.0, 74.4, 73.4, 72.5, 72.0, 71.7, 70.9, 68.8, 67.6, 67.2, 50.5, 50.2, 47.1, 46.1, 37.9, 29.8, 29.1, 28.1, 28.0, 27.5, 23.4. HRMS (ESI) m/z calcd for C$_{64}$H$_{69}$NO$_{11}$Na [M+Na]$^+$ 1050.4763, found 1050.4736.

Compound 19:

The compound 18 (420 mg, 0.41 mmol) was dissolved in a mixed solvent of DCM/H$_2$O (9:1, v/v, 15.2 mL). The reaction solution was cooled to 0° C., and 2, 3-dichloro-5, 6-dicyano-1,4-benzoquinone (DDQ) (186 mg, 0.82 mmol) was added. The reaction temperature was raised to room temperature and the reaction was continued for 3 h. The reaction solution was diluted with DCM, sequentially washed with 10% Na$_2$S$_2$O$_3$ solution and saturated NaHCO$_3$ solution, dried with Na$_2$SO$_4$, filtered, concentrated, separated and purified by column chromatography (petroleum ether/ethyl acetate, 1:1) to obtain a compound 19 (275 mg, 76%). [α]$^{22}_D$=13.8 (c 0.5, CH$_3$Cl). $^1$H NMR (400 MHz, Chloroform-d) δ 7.48-7.18 (m, 25H, Ar), 5.35 (s, 1H, H-2), 5.20 (d, J=15.5 Hz, 2H, COOCH$_2$Ph), 4.93 (d-like, J=10.7 Hz, 1H, ArCH), 4.78 (bs, 2H, H-1, ArCH), 4.74-4.46 (m, 6H, ArCH), 4.02-3.90 (m, 2H, H-6, H-5), 3.84 (m, 3H, H-3, H-4, H-7a), 3.65 (m, 3H, H-7b, OCH$_2$), 3.45-3.14 (m, 3H, OCH$_2$, NCH$_2$), 2.87-2.61 (m, 4H, C(O)CH2CH2(O)C), 2.17 (s, 3H, CH$_3$), 1.74-1.46 (m, 4H, CH$_2$CH$_2$), 1.32-1.17 (m, 2H, CH$_2$); $^{13}$C NMR (101 MHz, CDCl$_3$) δ 172.0, 137.9, 137.8, 128.6, 128.5, 128.4, 128.4, 128.1, 128.0, 127.9, 127.8, 127.7, 127.3, 127.2, 97.3 (C-1), 78.6, 75.0, 74.2, 72.0, 71.9, 71.7, 68.7, 67.9, 67.3, 50.5, 50.2, 47.1, 46.1, 38.1, 29.9, 29.1, 28.2, 28.0, 27.5, 23.4. HRMS (ESI) m/z calcd for C$_{53}$H$_{61}$NO$_{11}$Na [M+Na]$^+$ 910.4137, found 910.4117.

Compound 20:

The compound 19 (210 mg, 0.24 mmol) was dissolved in pyridine (2.3 mL), and acetic anhydride (0.45 mL, 4.74 mmol) and a catalytic amount of DMAP were added at 0° C. The reaction solution was returned to room temperature, stirred for 12 h, concentrated, separated and purified by column chromatography (petroleum ether/ethyl acetate, 3:1) to obtain a compound 20 (203 mg, 92%). [α]$^{22}_D$=20.4 (c 1.0, CH$_3$Cl). $^1$H NMR (400 MHz, Chloroform-d) δ 7.51-7.04 (m, 25H, Ar), 5.35 (d, J=3.1 Hz, 1H, H-2), 5.21 (d, J=14.5 Hz, 1H, COOCH$_2$Ph), 4.93 (d-like, J=10.7 Hz, 1H), 4.78-4.71 (m, 3H, H-1, ArCH), 4.67-4.47 (m, 5H, ArCH), 4.34 (dd, J=12.1, 3.5 Hz, 1H, H-7a), 4.27 (dd, J=12.0, 7.8 Hz, 1H, H-7b), 4.02 (dd, J=8.9, 4.0 Hz, 1H, H-5), 3.95 (dd, J=7.8, 3.5 Hz, 1H, H-6), 3.92 (m, 1H, H-3), 3.83 (dd, J=8.9, 8.9 Hz, 1H, H-4), 3.64 (m, 1H, OCH$_2$), 3.44-3.12 (m, 3H, OCH$_2$, NCH$_2$), 2.84-2.64 (m, 4H, C(O)CH$_2$CH$_2$(O)C), 2.19 (s, 3H, CH$_3$), 2.02 (s, 3H, OAc), 1.62-1.47 (m, 4H, CH$_2$CH$_2$), 1.38-1.18 (m, 2H, CH$_2$); $^{13}$C NMR (101 MHz, CDCl$_3$) δ 206.3, 172.0, 170.8, 138.3, 138.1, 137.9, 137.9, 128.6, 128.5, 128.5, 128.4, 128.4, 128.3, 128.2, 128.1, 128.1, 128.0, 127.9, 127.9, 127.9, 127.8, 127.8, 127.7, 127.6, 127.4, 127.3, 127.2, 97.4 (C-1), 78.6, 76.6, 75.0, 74.1, 72.1, 71.7, 71.7, 71.7, 68.6, 67.7, 67.2, 64.6, 50.6, 50.2, 47.1, 46.1, 38.0, 29.9, 29.8, 29.2, 28.2, 27.9, 27.5, 23.4, 23.4, 21.0. HRMS (ESI) m/z calcd for C$_{55}$H$_{63}$NO$_{12}$Na [M+Na]$^+$ 952.4242, found 952.4233.

Compound 21:

The compound 20 (190 mg, 0.2 mmol) was dissolved in a mixed solvent of DCM/MeOH (20:1, v/v, 4 mL), and hydrazine acetate (27.6 mg, 0.3 mmol) was added. The reaction solution was stirred at room temperature for 2 h.

The reaction solution was washed with NaHCO$_3$, dried with anhydrous Na$_2$SO$_4$, concentrated, separated and purified by column chromatography (petroleum ether/ethyl acetate, 3:1) to obtain a compound 21 (158 mg, 95%). [α]$^{22}_D$=34.5 (c 1.0, CH$_3$Cl). $^1$H NMR (400 MHz, Chloroform-d) δ 7.45-7.13 (m, 25H), 5.18 (d, J=14.0 Hz, 2H, COOCH$_2$Ph), 4.87 (d-like, J=10.8 Hz, 1H, ArCH), 4.81 (m, 1H, H-1), 4.76-4.45 (m, 7H, ArCH), 4.31 (dd, J=12.1, 3.8 Hz, 1H, H-7a), 4.25 (dd, J=12.1, 7.6 Hz, 1H, H-7b), 4.00 (s, 1H, H-2), 3.94-3.85 (m, 3H, H-3, H-5, H-6), 3.82 (dd, J=9.6, 8.4 Hz, 1H, H-4), 3.69-3.56 (m, 1H, OCH$_2$), 3.37-3.16 (m, 3H, OCH$_2$, NCH$_2$), 2.42 (bs, 1H, OH), 1.97 (s, 3H, OAc), 1.63-1.64 (m, 4H, CH$_2$CH$_2$), 1.37-1.13 (m, 2H, CH$_2$); $^{13}$C NMR (101 MHz, CDCl3) δ 170.8, 138.3, 138.1, 137.9, 137.8, 128.6, 128.6, 128.5, 128.4, 128.3, 128.3, 128.2, 128.2, 128.1, 128.0, 128.0, 127.9, 127.9, 127.9, 127.7, 127.6, 127.3, 127.2, 98.9 (C-1), 80.8, 76.4, 75.0, 74.1, 72.1, 72.0, 71.4, 68.1, 67.5, 67.2, 64.4, 50.5, 50.2, 47.1, 46.1, 29.1, 27.9, 27.5, 23.4, 21.0. HRMS (ESI) m/z calcd for C$_{50}$H$_{57}$NO$_{10}$Na [M+Na]$^+$ 854.3875, found 854.3863.

Embodiment 3

Figure 3:
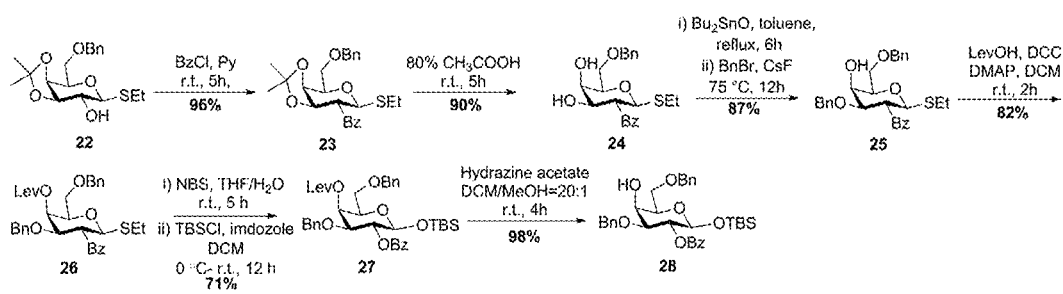
FIG. 3: Synthesis of sugar building block 28.

The synthesis route of the building block 28 is shown in FIG. 3.

As shown in FIG. 3, a compound 22 is used as a starting material, and 2-OH is protected with Bz to obtain a compound 23. The propylidene group of the compound 23 is opened under the action of 80% acetic acid to obtain a compound 24. 3-OH of the compound 24 is selectively protected with Bn to obtain a compound 25. 4-OH of the compound 25 is protected with Lev to obtain a compound 26. The thioglycoside 26 is hydrolyzed under a NBS condition to expose a terminal group OH, and the terminal group —OH is reacted with t-butyldimethylsilyl chloride (TBSCl) to obtain a galactose 27 with a fully protected terminal group by TBS. Lev is removed under the action of hydrazine acetate to obtain a galactose building block 28.

Specific test operations and steps are as follows.

Compound 23:

The compound 22 (4.2 g, 11.8 mmol) was dissolved in pyridine (59.5 mL) and stirred at 0° C. for 5 min. BzCl (2.78 mL, 24 mmol) and a catalytic amount of DMAP were added. The reaction solution was stirred at room temperature for 4 h. The reaction solution was sequentially washed with saturated NaHCO$_3$ and saturated brine, dried with anhydrous Na$_2$SO$_4$, concentrated and purified by column chromatography (petroleum ether/ethyl acetate, 10:1) to obtain a compound 23 (5.2 g, 96%). [α]$^{22}_D$=22.9 (c 1.0, CH$_3$Cl). $^1$H NMR (400 MHz, Chloroform-d) δ 8.10-7.94 (m, 2H, Ar), 7.60-7.51 (m, 1H, Ar), 7.45-7.42 (m, 2H, Ar), 7.38-7.27 (m, 5H, Ar), 5.28 (dd, J=9.9, 6.8 Hz, 1H, H-2), 4.66 (d-like, J=12.0 Hz, 1H, ArCH), 4.58 (d-like, J=12.0 Hz, 1H, ArCH), 4.53 (d, J=9.9 Hz, 1H, H-1), 4.34 (dd, J=6.8, 5.4 Hz, 1H, H-3), 4.30 (dd, J=5.4, 2.0 Hz, 1H, H-4), 4.03 (dt, J=6.1, 2.0 Hz, 1H, H-5), 3.83 (d, J=6.1 Hz, 2H, H-6a, H-6b), 2.89-2.57 (m, 2H, SCH$_2$CH$_3$), 1.61 (s, 3H, CH$_3$), 1.36 (s, 3H, CH$_3$), 1.25 (t, J=7.4 Hz, 3H, SCH$_2$CH$_3$); $^{13}$C NMR (101 MHz, CDCl$_3$) δ 165.5, 138.1, 133.1, 129.9, 129.8, 128.4, 128.3, 127.7, 127.7, 110.5, 82.9 (C-1), 77.1, 75.9, 73.9, 73.6, 72.2, 69.4, 27.8, 26.4, 24.3, 14.9. HRMS (ESI) m/z calcd for C$_{25}$H$_{31}$O$_6$SN [M+NH$_4$]$^+$ 476.2101, found 476.2104.

Compound 24:

The compound 23 (1.2 g, 2.6 mmol) was dissolved in 80% aqueous acetic acid (25 mL), and the reaction solution was stirred at 60° C. for 5 h. The TLC plate showed the complete reaction of the raw material. After concentration, the reaction solution was dissolved with DCM, washed with saturated $NaHCO_3$, dried with $Na_2SO_4$, filtered, concentrated, separated and purified by column chromatography (petroleum ether/ethyl acetate, 1:1) to obtain a compound 24 (0.98 g, 90%). $[\alpha]^{22}_D$=−19.4 (c 1.0, $CH_3Cl$). $^1H$ NMR (400 MHz, Chloroform-d) δ 8.11-7.90 (m, 2H, Ar), 7.63-7.51 (m, 1H, Ar), 7.49-7.41 (m, 2H, Ar), 7.39-7.28 (m, 5H, Ar), 5.30 (dd, J=9.6, 9.6 Hz, 1H, H-2), 4.60 (d, J=1.8 Hz, 2H, ArCH), 4.56 (d, J=9.6 Hz, 1H, H-1), 4.13 (ddd, J=3.6, 3.6, 1.1 Hz, 1H, H-4), 3.82 (m, 2H, H-6a, H-6b), 3.78 (dd, J=9.6, 3.6 Hz, 1H, H-3), 3.71 (dt, J=5.3, 1.1 Hz, 1H, H-5), 3.13 (d, J=7.9 Hz, 1H, OH), 3.03 (d, J=3.6 Hz, 1H, OH), 2.86-2.63 (m, 2H, $SCH_2CH_3$), 1.26 (t, J=7.4 Hz, 3H, $SCH_2CH_3$); $^{13}C$ NMR (101 MHz, $CDCl_3$) δ 166.8, 137.7, 133.3, 130.0, 129.7, 128.5, 128.4, 127.9, 127.8, 83.3 (C-1), 77.2, 73.9, 73.8, 72.3, 69.9, 69.6, 23.9, 15.0. HRMS (ESI) m/z calcd for $C_{22}H_{26}O_6SNa$ $[M+Na]^+$ 441.1342, found 441.1347.

Compound 25:

The compound 24 (4.2 g, 10.1 mmol) was dissolved in toluene (60 mL). $Bu_2SnO$ (3.8 g, 15.2 mmol) was added to a reaction flask, and the reaction solution was heated for reflux for 2 h and cooled to room temperature. TBAI (5.6 g, 15.2 mmol) and BnBr (1.8 g, 15.2 mmol) were added. The reaction solution was reacted at 65° C. overnight. The reaction solution was filtered through diatomite, concentrated, separated and purified by column chromatography (petroleum ether/ethyl acetate, 6:1) to obtain a compound 25 (4.5 g, 87%). $[\alpha]^{22}_D$=19.4 (c 1.0, $CH_3Cl$). $^1H$ NMR (400 MHz, Chloroform-d) δ 8.12-7.89 (m, 2H, Ar), 7.64-7.53 (m, 1H, Ar), 7.45 (dd, J=8.3, 7.2 Hz, 2H, Ar), 7.40-7.28 (m, 5H, Ar), 7.23-7.12 (m, 5H, Ar), 5.53 (dd, J=9.7, 9.7 Hz, 1H, H-2), 4.67 (d-like, J=12.3 Hz, 1H, ArCH), 4.60 (s, 2H, ArCH), 4.53 (d-like, J=12.3 Hz, 1H, ArCH), 4.48 (d, J=9.7 Hz, 1H, H-1), 4.19 (ddd, J=3.1, 1.5, 1.5 Hz, 1H, H-4), 3.83 (dd, J=9.8, 6.4 Hz, 1H, H-6a), 3.77 (dd, J=9.8, 5.7 Hz, 1H, H-6b), 3.67-3.69 (m, 1H, H-5), 3.65 (dd, J=9.7, 3.1 Hz, 1H, H-3), 2.81-2.65 (m, 2H, $SCH_2CH_3$), 2.64 (t, J=1.6 Hz, 1H), 1.22 (t, J=7.5 Hz, 3H, $SCH_2CH_3$); $^{13}C$ NMR (101 MHz, $CDCl_3$) δ 165.4, 137.9, 137.1, 133.1, 130.0, 129.9, 128.4, 128.4, 128.4, 128.3, 128.0, 127.8, 127.8, 83.5 (C-1), 79.3, 73.8, 71.3, 69.6, 69.0, 66.4, 23.6, 14.9. HRMS (ESI) m/z calcd for $C_{29}H_{32}O_6SNa$ $[M+Na]^+$ 531.1811, found 531.1819.

Compound 26:

The compound 25 (4.0 g, 7.9 mmol) was dissolved in DCM (150 mL). LevOH (1.36 g, 11.7 mmol), dicyclohexylcarbodiimide (DCC) (2.41 g, 11.7 mmol), and N,N-dimethylpyridine (DMAP) (1.43 mg, 11.7 mmol) were added. The reaction was stirred at room temperature for 2 h, concentrated, separated and purified by column chromatography (petroleum ether/ethyl acetate, 4:1) to obtain a compound 26 (3.9 g, 82%). $[\alpha]^{22}_D$=42.1 (c 1.0, $CH_3Cl$). $^1H$ NMR (400 MHz, Chloroform-d) δ 8.07-7.80 (m, 2H, Ar), 7.64-7.55 (m, 1H, Ar), 7.50-7.41 (m, 2H, Ar), 7.41-7.25 (m, 5H, Ar), 7.22-7.04 (m, 5H, Ar), 5.72 (dd, J=3.4, 1.1 Hz, 1H, H-4), 5.41 (dd, J=9.8, 9.8 Hz, 1H, H-2), 4.63 (d-like, J=12.7 Hz, 1H, ArCH), 4.54-4.51 (m, 3H, H-1, ArCH), 4.41 (d-like, J=12.7 Hz, 1H, ArCH), 3.80 (ddd, J=7.0, 5.6, 1.1 Hz, 1H, H-5), 3.66 (dd, J=9.4, 5.6 Hz, 1H, H-6a), 3.65 (dd, J=9.4, 3.0 Hz, 1H, H-6b), 3.56 (dd, J=9.4, 7.0 Hz, 1H, H-6b), 2.91-2.57 (m, 6H, $SCH_2CH_3$, $C(O)CH_2CH_2(O)C$), 2.18 (s, 3H, $CH_3$), 1.22 (t, J=7.4 Hz, 3H, $SCH_2CH_3$); $^{13}C$ NMR (101 MHz, $CDCl_3$) δ 206.4, 172.1, 165.4, 137.7, 137.3, 133.2, 130.0, 129.8, 128.5, 128.3, 128.3, 128.2, 128.0, 127.9, 127.7, 83.9 (C-1), 77.2, 76.2, 73.8, 70.7, 69.5, 68.0, 66.5, 38.1, 29.9, 28.1, 24.2, 14.9. HRMS (ESI) m/z calcd for $C_{34}H_{38}O_8SNa$ $[M+Na]^+$ 629.2180, found 629.2181.

Compound 27:

The compound 26 (317 mg, 0.52 mmol) was dissolved in $THF/H_2O$ (v/v, 1:1, 5 mL) and NBS (223 mg, 1.25 mmol) was added. The reaction was stirred at room temperature for 5 h. The reaction solution was washed with saturated $NaHCO_3$, dried with anhydrous $Na_2SO_4$, concentrated and purified by column chromatography to obtain an intermediate (225 mg). The intermediate was dissolved in dry DCM (2.5 mL). The reaction solution was cooled to 0° C., imidazole (75 mg, 1.11 mmol) and TBSCl (84 mg, 0.56 mmol) were added. The reaction was stirred at room temperature for 12 h. The reaction solution was quenched with saturated $NH_4Cl$. The mixture was extracted with DCM three times. The organic phase was washed with water, dried with anhydrous $Na_2SO_4$, concentrated and purified by column chromatography (petroleum ether/ethyl acetate, 20:1) to obtain a compound 27 (248 mg, 71%). $[\alpha]^{22}_D$=44.8 (c 1.0, $CH_3Cl$). $^1H$ NMR (400 MHz, Chloroform-d) δ 8.02-7.80 (m, 2H, Ar), 7.64-7.50 (m, 1H, Ar), 7.45 (t, J=7.7 Hz, 2H, Ar), 7.39-7.27 (m, 5H, Ar), 7.20-7.04 (m, 5H, Ar), 5.65 (dd, J=3.2, 0.8 Hz, 1H, H-4), 5.34 (dd, J=10.1, 7.7 Hz, 1H, H-2), 4.71 (d, J=7.7 Hz, 1H, H-1), 4.63 (d-like, J=12.9 Hz, 1H, ArCH), 4.54 (s, 2H, ArCH), 4.40 (d-like, J=12.9 Hz, 1H, ArCH), 3.76 (t, J=6.2 Hz, 1H, H-5), 3.68-3.61 (m, 2H, H-6a, H-6b), 3.59 (dd, J=10.1, 3.2 Hz, 1H, H-3), 2.88-2.64 (m, 4H, $C(O)CH_2CH_2(O)C$), 2.19 (s, 3H, $CH_3$), 0.75 (s, 9H, OTBS), 0.06 (s, 3H, OTBS), −0.02 (s, 3H, OTBS); $^{13}C$ NMR (101 MHz, $CDCl_3$) δ 206.6, 172.1, 165.3, 137.8, 137.5, 133.0, 130.1, 129.8, 128.5, 128.3, 128.2, 128.1, 127.9, 127.8, 127.6, 96.3 (C-1), 76.1, 73.8, 73.1, 72.5, 70.6, 68.2, 66.4, 38.1, 29.9, 28.2, 25.4, 17.8, −4.2, −5.3. HRMS (ESI) m/z calcd for $C_{34}H_{38}O_9SiNa$ $[M+Na]^+$ 699.2960, found 699.2957.

Compound 28:

The compound 27 (203 mg, 0.30 mmol) was dissolved in a mixed solvent of DCM/MeOH (20:1, v/v, 3.5 mL). and hydrazine acetate (41.4 mg, 0.45 mmol) was added. The reaction solution was stirred at room temperature for 4 h. The reaction solution was washed with $NaHCO_3$, dried over anhydrous $Na_2SO_4$, concentrated, separated and purified by column chromatography (petroleum ether/ethyl acetate, 6:1) to obtain a compound 28. $[\alpha]^{22}_D$=18.6 (c 1.0, $CH_3Cl$). $^1H$ NMR (400 MHz, Chloroform-d) δ 8.00 (m, 2H, Ar), 7.63-7.53 (m, 1H, Ar), 7.49-7.40 (m, 2H, Ar), 7.39-7.26 (m, 5H, Ar), 7.25-7.09 (m, 5H, Ar), 5.42 (dd, J=9.8, 7.6 Hz, 1H, H-2), 4.71 (d, J=7.7 Hz, 1H, H-1), 4.69 (d-like, J=12.4 Hz, 1H, ArCH), 4.61 (s, 2H, ArCH), 4.52 (d-like, J=12.5 Hz, 1H), 4.13 (dd, J=3.4, 1.4 Hz, 1H, H-4), 3.87 (dd, J=9.8, 6.0 Hz, 1H, H-6a), 3.75 (dd, J=9.8, 6.0 Hz, 1H, H-6b), 3.65 (t, J=6.0 Hz, 1H, H-5), 3.59 (dd, J=9.8, 3.3 Hz, 1H, H-3), 2.60 (t, J=1.6 Hz, 1H, OH), 0.74 (s, 9H, OTBS), 0.07 (s, 3H, OTBS), −0.01 (s, 3H, OTBS). $^{13}C$ NMR (101 MHz, $CDCl_3$) δ 165.3, 138.1, 137.2, 132.9, 130.2, 129.8, 128.5, 128.4, 128.3, 127.9, 127.9, 127.8, 96.3 (C-1), 78.1, 73.8, 73.6, 73.2, 71.1, 69.2, 66.2, 25.5, 17.8, −4.2, −5.3. HRMS (ESI) m/z calcd for $C_{33}H_{42}O_7SiNa$ $[M+Na]^+$ 601.2592, found 601.2586.

Embodiment 4

The conditions of the glycosylation reaction and the conditions for removing acyl protection groups are as follows.

If not stated in the present disclosure, the conditions of the glycosylation reaction are as follows. The glycosyl donor and acceptor are co-distilled three times in toluene. Dry DCM or $DCM/Et_2O$ (v/v, 1:2) is added at the reaction concentration of 0.02-0.05 M and an activated 3 Å or 4 Å molecular sieve. Thiophene, being 10 equivalents of glycosyl donor, is added. The mixture is stirred at room temperature for 30 min and then cooled to 0° C. TMSOTf is added as a promoter and the reaction time is 3-5 h. After the completion of reaction, the reaction is terminated with pyridine. The reaction solution is filtered and diluted with DCM. After that, the solution is washed with saturated NaHCO$_3$, dried over anhydrous Na$_2$SO$_4$, concentrated, separated and purified by column chromatography.

If not stated in the present disclosure, the alkaline conditions for removing acyl are as follows. The starting material is dissolved in DCM/MeOH (v/v, 1:1) at a reaction concentration of 0.05 M and 0.5 equivalents of MeONa (5M in MeOH) is added. The reaction temperature is room temperature, and the TLC plate shows the completion of the reaction. The reaction solution is neutralized with Amerlite IR 120 (H$^+$) resin to pH 7, filtered, concentrated and purified by column chromatography.

Embodiment 5

Figure 4:
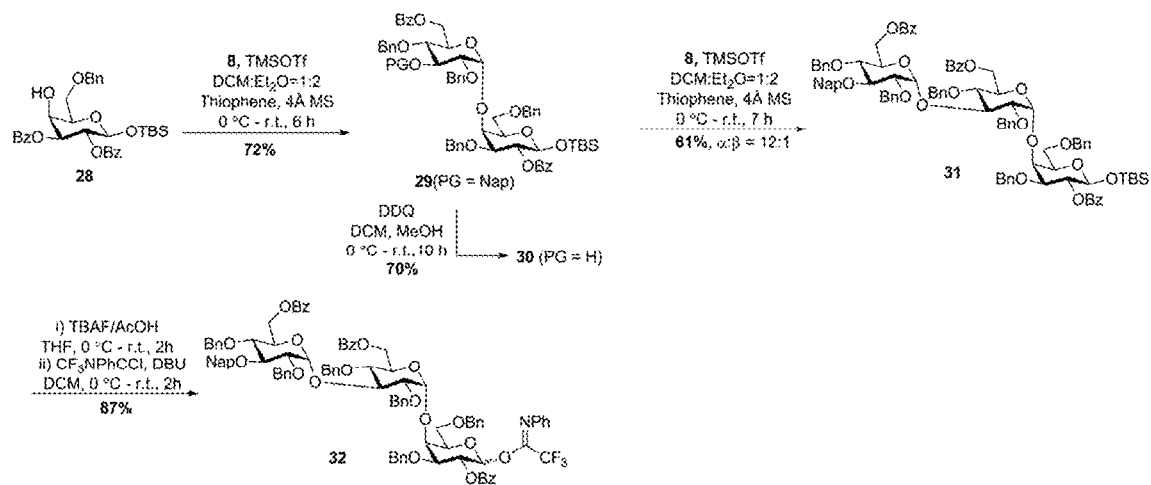
FIG. 4: Assembly of trisaccharide donor 32.

The assembly route of the trisaccharide donor 32 is shown in FIG. 4.

Specific test operations and steps are as follows.

Compound 29:

According to reaction condition 4.1, a glycosyl donor 8 (335 mg, 0.43 mmol) and a glycosyl acceptor 28 (301 mg, 0.52 mmol) were reacted to obtain 29 (361 mg, 72%). $[\alpha]^{22}_D$=93.1 (c 1.0, CH$_3$Cl). $^1$H NMR (400 MHz, Chloroform-d) δ 8.09-7.94 (m, 4H, Ar), 7.85-7.67 (m, 4H, Ar), 7.63-7.11 (m, 28H), 5.55 (dd, J=10.2, 7.5 Hz, 1H, H-2b), 5.11 (d, J=3.8 Hz, 3H, H-1a, 2×ArCH), 4.97 (t-like, J=11.3 Hz, 2H, ArCH), 4.77 (d, J=7.5 Hz, 1H, H-1b), 4.78-4.73 (m, 2H, ArCH), 4.68 (d-like, J=11.2 Hz, 1H, ArCH), 4.62-4.50 (m, 2H, H-5a, ArCH), 4.39 (dd, J=9.4, 9.4 Hz, 1H, H-3a), 4.33-4.18 (m, 5H, H-6a, H-6a', H-4b, 2×ArCH), 4.10-3.99 (m, 1H, H-6b), 3.79 (t, J=9.4 Hz, 1H, H-4a), 3.63 (dd, J=10.1, 3.9 Hz, 2H, H-2a), 3.60-3.51 (m, 3H, H-6b', H-3b, H-5b), 0.80 (s, 9H, OTBS), 0.22 (s, 3H, OTBS), 0.10 (s, 3H, OTBS); $^{13}$C NMR (101 MHz, cdcl$_3$) δ 166.02, 165.19, 138.61, 138.22, 137.91, 137.47, 136.04, 133.35, 132.95, 132.82, 132.79, 130.39, 130.17, 129.78, 129.63, 128.37, 128.33, 128.29, 128.25, 128.22, 128.12, 127.99, 127.90, 127.69, 127.67, 127.66, 127.63, 127.60, 127.55, 127.38, 127.05, 126.96, 126.31, 125.89, 125.77, 99.46 (C-1a), 96.92 (C-1b), 81.81, 80.84, 77.79, 77.73, 75.90, 74.57, 74.05, 73.77, 73.69, 73.14, 71.44, 69.36, 67.64, 63.08, 25.67, 17.88, −3.84, −4.27. HRMS (ESI) m/z calcd for C$_{71}$H$_{76}$O$_{13}$SiNa [M+Na]$^+$ 1187.4947, found 1187.4907.

Compound 30:

The compound 29 (940 mg, 0.81 mmol) was dissolved in a mixed solvent of DCM/MeOH (9:1, v/v, 18 mL). The reaction solution was cooled to 0° C. and 2, 3-dichloro-5, 6-dicyano-1,4-benzoquinone (DDQ) (545 mg, 2.4 mmol) was added. The reaction temperature was raised to room temperature and the reaction was continued for 10 h. The reaction solution was diluted with DCM, sequentially washed with 10% Na$_2$S$_2$O$_3$ solution and saturated NaHCO$_3$ solution, dried over Na$_2$SO$_4$, filtered, concentrated, separated and purified by column chromatography (petroleum ether/ethyl acetate, 1:1) to obtain a compound 30 (581 mg, 70%). $[\alpha]^{22}_D$=75.6 (c 1.0, CH$_3$Cl). $^1$H NMR (400 MHz, Chloroform-d) δ 8.04-7.92 (m, 4H, Ar), 7.60-7.51 (m, 2H, Ar), 7.48-7.27 (m, 16H, Ar), 7.22-7.11 (m, 8H, Ar), 5.46 (dd, J=10.3, 7.5 Hz, 1H, H-2b), 5.08 (d, J=3.4 Hz, 1H, H-1a), 4.86-4.77 (m, 2H, ArCH), 4.71 (d, J=7.6 Hz, 1H, H-1b), 4.75-4.68 (m, 3H, ArCH), 4.56-4.48 (dd, 2H, H-5a, ArCH), 4.44 (dd, J=9.4, 9.4 Hz, 1H, H-3a), 4.24-4.26 (d, 3H, H-6a, 2×ArCH), 4.24-4.19 (m, 2H, H-6a', H-4b), 3.96 (dd, J=9.3, 7.7 Hz, 1H, H-4a), 3.70-3.61 (m, 1H, H-6b), 3.62-3.47 (m, 3H, H-3b, H-5b, H-6b'), 3.46 (dd, J=10.1, 3.4 Hz, 1H, H-2a), 0.76 (s, 9H, OTBS), 0.10 (s, 3H, OTBS), 0.00 (s, 3H, OTBS); $^{13}$C NMR (101 MHz, CDCl$_3$) δ 166.1, 165.1, 138.4, 138.3, 137.9, 137.4, 132.9, 132.8, 130.3, 130.2, 129.8, 129.7, 128.5, 128.4, 128.4, 128.3, 128.3, 128.1, 127.8, 127.7, 127.6, 127.5, 98.9 9 (C-1a), 96.7 (C-1b), 80.3, 77.8, 77.5, 73.9, 73.8, 73.6, 73.5, 73.3, 73.1, 72.8, 71.4, 68.8, 67.7, 63.2, 25.6, 17.9, −4.1, −4.9. HRMS (ESI) m/z calcd for C$_{60}$H$_{68}$O$_{13}$SiNa [M+Na]$^+$ 1047.4321, found 1047.4304.

Compound 31:

According to reaction conditions 4.1, a glycosyl donor 8 (100 mg, 0.13 mmol) and a glycosyl acceptor 30 (87.3 g, 0.085 mmol) were reacted to obtain a compound 31 (78 mg, 57%). $[\alpha]^{22}_D$=93.4 (c 1.0, CH$_3$Cl). $^1$H NMR (400 MHz, Chloroform-d) δ 8.10-7.98 (m, 8H, Ar), 7.85-7.68 (m, 4H, Ar), 7.62-7.04 (m, 40H, Ar), 5.68 (d, J=3.5 Hz, 1H, H-1a), 5.55 (dd, J=10.3, 7.5 Hz, 1H, H-2c), 5.15 (d, J=3.1 Hz, 1H, H-1b), 5.13-5.06 (m, 2H, ArCH), 4.99 (d-like, J=10.9 Hz, 1H, ArCH), 4.89-4.82 (d-like, J=10.9, 1H, ArCH), 4.80 (d, J=7.6 Hz, 1H, H-1c), 4.79-4.62 (m, 8H, H-3b, H-5b, 6×ArCH), 4.56-4.48 (m, 3H, H-5a, 2×ArCH), 4.47-4.38 (m, 2H, H-6a, H-6b), 4.37-4.23 (m, 3H, H-6a', H-3b, ArCH), 4.22-4.13 (m, 3H, H-3a, H-6b', H-3c), 4.03-3.95 (m, 2H, H-4b, H-6c), 3.72 (dd, J=10.4, 9.2 Hz, 1H, H-4a), 3.67 (dd, J=10.1, 3.1 Hz, 1H, H-2a), 3.64-3.52 (m, 4H, H-2b, H-3c, H-5c, H-6c'), 0.75 (s, 9H, OTBS), 0.20 (s, 3H, OTBS), 0.09 (s, 3H, OTBS); $^{13}$C NMR (101 MHz, CDCl$_3$) δ 166.1, 166.0, 165.0, 138.3, 138.2, 138.0, 137.9, 137.6, 137.4, 136.1, 133.3, 132.9, 132.9, 132.8, 132.7, 130.4, 130.2, 130.2, 129.8, 129.7, 129.7, 129.1, 128.4, 128.4, 128.4, 128.3, 128.3, 128.3, 128.2, 128.1, 128.0, 128.0, 127.9, 127.9, 127.8, 127.7, 127.7, 127.6, 127.5, 127.2, 127.1, 126.6, 126.1, 126.0, 125.8, 125.3, 98.6 (C-1b), 97.0 (C-1a), 96.8 (C-1c), 82.3, 80.0, 79.9, 78.6, 78.2, 77.7, 75.8, 75.1, 75.0, 74.7, 73.8, 73.6, 73.5, 73.5, 73.2, 71.9, 71.6, 68.7, 68.4, 68.2, 63.2, 63.1, 25.5, 17.8, −3.8, −4.4. HRMS (ESI) m/z calcd for C$_{98}$H$_{102}$O$_{19}$SiNa [M+Na]$^+$ 1633.6677, found 1633.6667.

Compound 32:

The compound 31 (54.0 mg, 0.034 mmol) was dissolved in THF (1.7 mL) and cooled to 0° C. AcOH (19.4 μL, 0.34 mmol) was added and followed by 1 M TBAF in THF (0.34 mL, 0.34 mmol). The solution was stirred at room temperature for 2 h. The reaction solution was diluted with ethyl acetate, then washed with water three times, dried over anhydrous Na$_2$SO$_4$, concentrated, separated and purified by column chromatography to obtain an intermediate. The intermediate was dissolved in dry DCM and cooled to 0° C. N-phenyltrifluoroacetyl chloride (20 uL, 0.14 mmol) and DBU (12.6 uL, 0.084 mmol) were added. The reaction solution was stirred at room temperature for 2 h, concentrated, separated and purified by column chromatography to obtain a compound 32 (49.3 mg, 87%). $[\alpha]^{22}_D$=122.6 (c 1.0, CH$_3$Cl). $^1$H NMR (400 MHz, Chloroform-d) δ 8.08-7.94 (m, 6H, Ar), 7.87-6.52 (m, 51H, Ar), 5.96 (bs, 1H, H-1c), 5.76 (dd, J=8.7, 8.7 Hz, 1H, H-2c), 5.67 (d, J=3.6 Hz, 1H, H-1a), 5.15-5.04 (m, 3H, H-1b, 2×ArCH), 4.99 (d-like, J=10.9 Hz, 1H, ArCH), 4.85 (d-like, J=10.8 Hz, 1H, ArCH), 4.81-4.67 (m, 4H, ArCH), 4.67-4.47 (m, 8H, H-5a, H-6a, H-3b, H-5b, 4×ArCH), 4.47-4.28 (m, 3H, H-6a', H-6b', ArCH), 4.28-4.09 (m, 4H, H-3a, H-6b', H-4c, H-4b), 3.99-3.85 (m, 2H, H-4b, H-6c), 3.82-3.51 (m, 5H, H-2a, H-4a, H-2b, H-3c, H-5c, H-6c'); $^{13}$C NMR (101 MHz, CDCl$_3$) δ 166.1, 164.7, 138.2, 138.1, 137.9, 137.9, 137.5, 137.0, 136.0, 133.3, 133.2, 133.0, 132.9, 132.9, 130.1, 130.0, 129.9, 129.7, 129.6, 129.4, 128.6, 128.5, 128.5, 128.4, 128.4, 128.3, 128.3, 128.3, 128.1, 128.1, 128.0, 128.0, 128.0, 127.9, 127.9, 127.8, 127.8, 127.7, 127.7, 127.7, 127.6, 127.3, 127.2, 126.6, 126.0, 126.0, 125.8, 120.4, 119.3, 98.6 (C-1a), 97.2 (C-1b), 95.2 (C-1c), 82.4, 80.0, 79.9, 78.7, 77.8, 75.8, 75.3, 75.1, 73.8, 73.2, 71.8, 69.1, 68.9, 63.2, 63.0. HRMS (ESI) m/z calcd for $C_{10}H_{92}F_3NO_{19}Na$ $[M+Na]^+$ 1690.6108, found 1690.6102.

Embodiment 6

Figure 5:
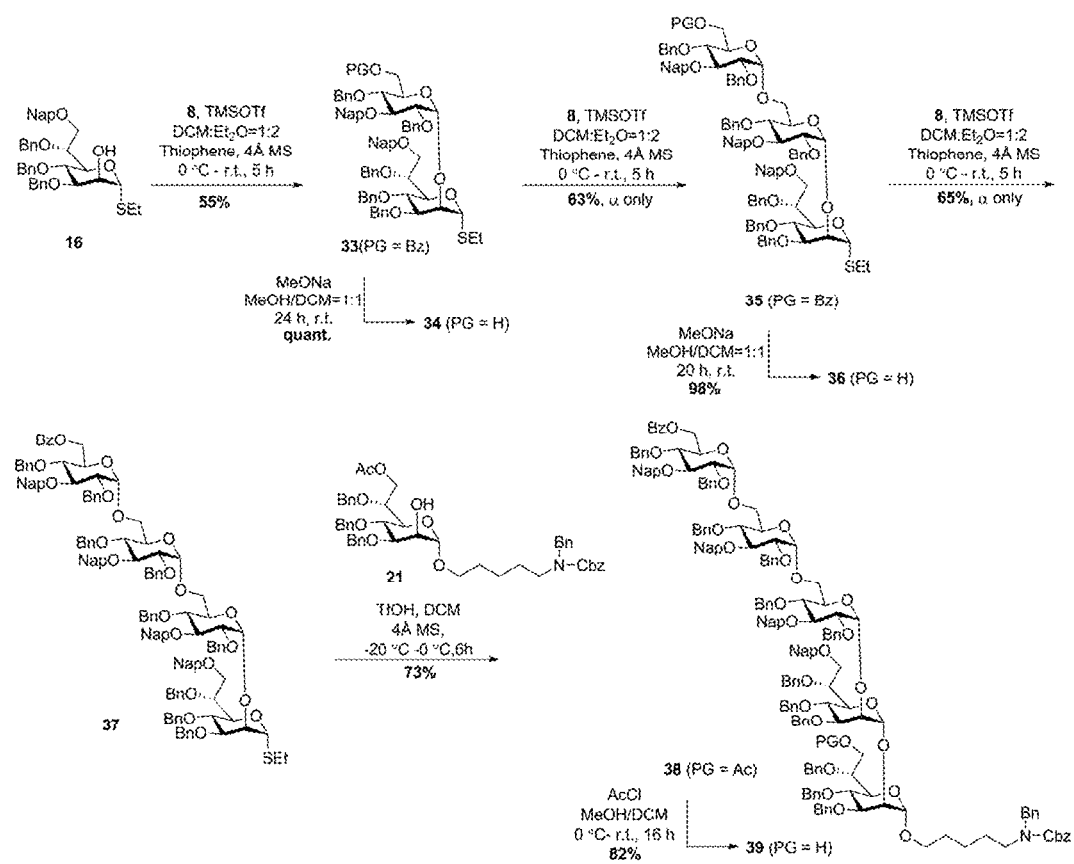
FIG. 5: Assembly of pentasaccharide acceptor 42.

The assembly route of the pentasaccharide acceptor 39 is shown in FIG. 5.

Specific test operations and steps are as follows.

Compound 33:

According to reaction conditions 4.1, a glycosyl donor 8 (1.32 g, 1.7 mmol) and a glycosyl acceptor 16 (1.33 g, 2.0 mmol) were reacted to obtain a compound 33 (1.17 mg, 55%). $[\alpha]^{22}_D$=71.9 (c 1.0, $CH_3Cl$). $^1H$ NMR (400 MHz, Chloroform-d) δ 8.09-8.03 (m, 2H, Ar), 7.85-7.51 (m, 10H, Ar), 7.47-7.05 (m, 32H, Ar), 5.46 (d, J=3.6 Hz, 1H, H-1a), 5.37 (d, J=1.7 Hz, 1H, H-1b), 5.03-4.86 (m, 3H, ArCH), 4.81-4.60 (m, 9H, ArCH), 4.59 (m, 1H, H-6a), 4.53-4.43 (m, 3H, H-6a', 2×ArCH), 4.35-4.24 (m, 3H, H-4b, H-5b, H-2b), 4.19 (ddd, J=10.0, 5.5, 1.9 Hz, 1H, H-5a), 4.12 (dd, J=9.2, 9.2 Hz, 1H, H-3a), 4.02 (dd, J=7.0, 4.7 Hz, 1H, H-6b), 3.93 (dd, J=8.6, 2.6 Hz, 1H, H-3b), 3.85 (dd, J=10.5, 4.7 Hz, 1H, H-7b), 3.77 (dd, J=10.4, 7 Hz, 1H, H-7b'), 3.63-3.53 (m, 2H, H-2a, H-4a), 2.65-2.43 (m, 2H, $SCH_2CH_3$), 1.20 (t, J=7.4 Hz, 3H, $SCH_2CH_3$); $^{13}C$ NMR (101 MHz, $CDCl_3$) δ 166.3, 138.9, 138.5, 138.4, 137.7, 137.7, 136.1, 136.1, 133.3, 133.3, 133.1, 132.9, 132.9, 129.8, 129.8, 128.5, 128.5, 128.4, 128.2, 128.2, 128.2, 128.0, 128.0, 127.9, 127.9, 127.8, 127.6, 127.6, 127.5, 127.3, 127.3, 127.2, 126.5, 126.0, 126.0, 125.9, 125.9, 125.8, 125.6, 125.6, 97.1 (C-1a), 83.8 (C-1b), 81.8, 81.4, 79.8, 79.1, 77.8, 75.8, 75.4, 75.1, 74.6, 74.6, 73.3, 72.9, 72.8, 72.6, 71.5, 71.5, 69.6, 63.9, 25.4, 14.9. HRMS (ESI) m/z calcd for $C_{79}H_{78}O_{12}SNa$ $[M+Na]^+$ 1273.5106, found 1273.5109.

Compound 34:

According to reaction conditions 4.2, the ester group of the compound 33 (180 mg, 0.14 mmol) was removed to obtain a compound 34 (161 mg, eq.). $[\alpha]^{22}_D$=101.2 (c 1.0, $CH_3Cl$). $^1H$ NMR (400 MHz, Chloroform-d) δ 7.81-7.56 (m, 8H, Ar), 7.46-7.05 (m, 31H, Ar), 5.40 (d, J=3.6 Hz, 1H, H-1a), 5.33 (d, J=1.7 Hz, 1H, H-1b), 4.98-4.86 (m, 3H, ArCH), 4.80-4.55 (m, 9H, ArCH), 4.48 (t-like, J=11.0 Hz, 2H, ArCH), 4.30-4.21 (m, 2H, H-4b, H-5b), 4.18 (dd, J=1.7, 2.2 Hz, 1H, H-2b), 4.07 (dd, J=9.3, 9.3 Hz, 1H, H-3a), 4.01 (dd, J=6.9, 4.7 Hz, 1H, H-6b), 3.92 (dd, J=8.3, 2.2 Hz, 1H, H-3b), 3.89-3.71 (m, 5H, H-5a, H-6a, H-6a', H-7b, H-7b'), 3.59-3.48 (m, 2H, H-2, H-4), 2.72-2.51 (m, 2H, $SCH_2CH_3$), 1.67 (dd, J=7.4, 5.3 Hz, 1H, OH), 1.26 (t, J=7.4 Hz, 3H, $SCH_2CH_3$); $^{13}C$ NMR (101 MHz, $CDCl_3$) δ 138.9, 138.5, 138.4, 138.1, 137.8, 136.3, 136.1, 133.3, 133.3, 132.9, 128.5, 128.2, 128.2, 128.1, 127.9, 127.9, 127.9, 127.9, 127.8, 127.6, 127.5, 127.3, 127.3, 126.3, 126.1, 125.9, 125.9, 125.7, 125.6, 125.6, 97.4 (C-1a), 83.7 (C-1b), 81.7, 81.4, 79.8, 79.1, 75.6, 75.3, 75.1, 74.9, 74.6, 73.3, 73.0, 72.9, 72.5, 71.6, 71.5, 71.5, 62.0, 25.5, 15.1. HRMS (ESI) m/z calcd for $C_{72}H_{74}O_{11}SNa$ $[M+Na]^+$ 1169.4844, found 1169.4828.

Compound 35:

According to reaction conditions 4.1, a glycosyl donor 8 (350 mg, 0.46 mmol) and a glycosyl acceptor 37 (400 mg, 0.35 mmol) were reacted to obtain a compound 35 (380 mg, 63%). $[\alpha]^{22}_D$=48.8 (c 1.0, $CH_3Cl$). $^1H$ NMR (400 MHz, Chloroform-d) δ 8.01-7.94 (m, 2H, Ar), 7.83-7.58 (m, 13H, Ar), 7.54-7.04 (m, 46H, Ar), 5.42 (d, J=3.6 Hz, 1H, H-1b), 5.36 (d, J=1.7 Hz, 1H, H-1c), 5.03 (d-like, J=11.1 Hz, 1H, ArCH), 5.00 (d, J=3.5 Hz, 1H, H-1a), 4.98-4.86 (m, 4H, ArCH), 4.77-4.58 (m, 12H, ArCH), 4.57-4.53 (m, 1H, H-6a), 4.52-4.37 (m, 3H, H-6a', 2×ArCH), 4.35-4.26 (m, 3H, H-2c, H-5c, ArCH), 4.25-4.17 (m, 2H, H-3a, H-4c), 4.14 (ddd, J=10.3, 4.8, 2.0 Hz, 1H, H-5a), 4.06 (dd, J=9.3, 9.3 Hz, 1H, H-3b), 4.03-3.95 (m, 2H, H-5b, H-6c), 3.91 (dd, J=8.8, 2.3 Hz, 1H, H-3c), 3.90-3.79 (m, 2H, H-6b, H-7c), 3.81-3.69 (m, 2H, H-6b', H-7c'), 3.66-3.59 (m, 2H, H-2a, H-4a), 3.56 (dd, J=9.3, 9.3 Hz, 1H, H-4b), 3.36 (dd, J=9.3, 3.6 Hz, 1H, H-2b), 2.70-2.50 (m, 2H, $SCH_2CH_3$), 1.19 (t, J=7.4 Hz, 3H, $SCH_2CH_3$); $^{13}C$ NMR (101 MHz, $CDCl_3$) δ 166.2, 138.9, 138.6, 138.4, 138.4, 138.2, 137.9, 137.8, 136.4, 136.2, 136.1, 133.4, 133.3, 133.3, 133.0, 133.0, 132.9, 132.9, 130.0, 129.6, 128.4, 128.4, 128.4, 128.2, 128.2, 128.1, 128.1, 128.0, 127.9, 127.9, 127.9, 127.8, 127.8, 127.7, 127.6, 127.6, 127.5, 127.3, 127.2, 127.2, 126.7, 126.3, 126.2, 126.0, 126.0, 125.9, 125.8, 125.7, 125.6, 125.6, 96.7 (C-1a, C-1b), 83.9 (C-1c), 81.9, 81.8, 80.4, 79.8, 79.3, 75.8, 75.6, 75.3, 75.1, 74.6, 73.4, 73.2, 72.8, 72.7, 72.5, 72.5, 71.6, 71.2, 71.1, 68.9, 66.0, 63.6, 25.5, 15.0. HRMS (ESI) m/z calcd for $C_{110}H_{108}O_{17}SNa$ [M+Na]+ 1755.7199, found 1755.7195.

Compound 36:

According to reaction conditions 4.2, the ester group of the compound 35 (58 mg, 0.033 mmol) was removed to obtain a compound 36 (52.6 mg, 98%). $[\alpha]^{22}_D$=73.2 (c 1.0, $CH_3Cl$). $^1H$ NMR (400 MHz, Chloroform-d) δ 7.82-7.66 (m, 13H, Ar), 7.48-7.02 (m, 43H, Ar), 5.41 (d, J=3.6 Hz, 1H, H-1b), 5.36 (d, J=1.7 Hz, 1H, H-1c), 5.13 (d-like, J=11.2 Hz, 1H, ArCH), 5.00 (d, J=3.4 Hz, 1H, H-1a), 5.00-4.89 (m, 5H, ArCH), 4.76-4.44 (m, 13H, ArCH), 4.36 (d-like, J=12.0 Hz, 1H, ArCH), 4.32-4.20 (m, 3H, H-1c, H-4c, H-5c), 4.12 (dd, J=8.5, 8.5 Hz, 1H, H-3a), 4.08 (dd, J=8.7, 8.7 Hz, 1H, H-3b), 4.03-3.96 (m, 2H, H-5b, H-6c), 3.95-3.87 (m, 2H, H-6b, H-3c), 3.84 (dd, J=10.5, 4.6 Hz, 1H, H-7c), 3.81-3.64 (m, 6H, H-5a, H-6a, H-6a', H-4b, H-6b', H-7c'), 3.60-3.53 (m, 2H, H-2a, H-4a), 3.44 (dd, J=9.6, 3.6 Hz, 1H, H-2b), 2.69-2.53 (m, 2H, $SCH_2CH_3$), 1.22 (t, J=7.4 Hz, 3H, $SCH_2CH_3$). $^{13}C$ NMR (101 MHz, $CDCl_3$) δ 138.9, 138.6, 138.5, 138.4, 138.3, 138.3, 137.8, 136.4, 136.4, 136.1, 133.3, 133.3, 133.3, 132.9, 132.9, 132.9, 128.5, 128.4, 128.3, 128.2, 128.1, 128.1, 128.0, 128.0, 127.9, 127.9, 127.8, 127.8, 127.7, 127.7, 127.6, 127.6, 127.5, 127.3, 127.2, 127.2, 126.5, 126.4, 126.1, 126.0, 125.9, 125.9, 125.7, 125.7, 125.6, 125.6, 97.2 (C-1a), 97.0 (C-1b), 83.8 (C-1c), 81.8, 81.7, 80.3, 79.9, 79.2, 77.7, 75.6, 75.6, 75.3, 75.1, 75.0, 74.6, 73.8, 73.2, 72.8, 72.5, 72.4, 71.5, 71.4, 71.3, 70.9, 66.2, 62.0, 25.5, 15.0. HRMS (ESI) m/z calcd for $C_{103}H_{104}O_{16}SNa$ $[M+Na]^+$ 1651.6937, found 1651.6931.

Compound 37:

According to reaction conditions 4.1, a glycosyl donor 8 (163 mg, 0.21 mmol) and a glycosyl acceptor 36 (257 mg, 0.16 mmol) were reacted to obtain 37 (230 mg, 65%). $[\alpha]^{22}_D$=133.8 (c 1.0, $CH_3Cl$). $^1H$ NMR (400 MHz, Chloroform-d) δ 8.02-7.92 (m, 2H, Ar), 7.85-7.01 (m, 76H, Ar), 5.42 (d, J=3.6 Hz, 1H, H-1c), 5.34 (d, J=1.7 Hz, 1H, H-1d), 5.13 (d, J=3.6 Hz, 1H, H-1a), 5.13-5.08 (m, 2H, ArCH), 5.01-4.87 (m, 8H, H-1b, 7×ArCH), 4.81-4.52 (m, 15H, ArCH), 4.52-4.37 (m, 3H, H-6a, H-6a', ArCH), 4.35-4.17 (m, 4H, H-2d, H-4d, H-5d), 4.16-4.04 (m, 3H, H-3a, H-3b, H-3c), 4.04-3.90 (m, 5H, H-5a, H-5c, H-6c, H-3d, H-6d), 3.88-3.80 (m, 4H, H-4a, H-5c, H-6b, H-7d), 3.81-

3.66 (m, 4H, H-4b, H-6b', H-6c', H-7d'), 3.64 (dd, J=10.1, 8.9 Hz, 1H, H-4c), 3.59 (dd, J=9.6, 3.5 Hz, 1H, H-2a), 3.45 (dd, J=10.0, 3.5 Hz, 1H, H-2c), 3.43 (dd, J=10.0, 3.5 Hz, 1H, H-2b), 2.73-2.39 (m, 2H, SCH$_2$CH$_3$), 1.17 (t, J=7.4 Hz, 3H, SCH$_2$CH$_3$); $^{13}$C NMR (101 MHz, CDCl$_3$) δ 166.2, 138.9, 138.6, 138.5, 138.4, 138.3, 137.9, 137.8, 136.5, 136.1, 136.0, 133.3, 133.3, 133.3, 133.0, 132.9, 132.9, 132.9, 129.9, 129.6, 128.4, 128.4, 128.4, 128.4, 128.2, 128.2, 128.1, 128.1, 128.0, 127.9, 127.9, 127.8, 127.8, 127.7, 127.7, 127.6, 127.5, 127.5, 127.5, 127.3, 127.2, 127.1, 126.8, 126.5, 126.3, 126.2, 126.2, 126.0, 126.0, 125.9, 125.9, 125.9, 125.8, 125.6, 125.6, 97.2 (C-1c), 97.1 (C-1a, C-1b), 83.9 (C-1d), 81.8, 80.5, 80.3, 80.0, 79.2, 75.8, 75.6, 75.3, 75.1, 74.6, 73.7, 73.2, 72.8, 72.5, 72.4, 72.1, 71.5, 71.4, 70.9, 68.9, 66.1, 65.4, 63.3, 29.7, 25.5, 15.0. HRMS (ESI) m/z calcd for C$_{141}$H$_{138}$O$_{22}$SNa [M+Na]$^+$ 2237.9292, found 2237.9287.

Compound 38:

According to reaction conditions 4.1, a glycosyl donor 37 (150 mg, 0.068 mmol) and a glycosyl acceptor 21 (113 mg, 0.136 mmol) were reacted in the presence of NIS (30.6 mg, 0.136 mmol) and TfOH (0.88 uL, 0.01 mmol) to obtain a compound 38 (148 mg, 73%), wherein the reaction temperature was −20° C.-0° C. and the reaction time was 6 h. [α]$^{22}_D$=62.5 (c 1.0, CH$_3$Cl). $^1$H NMR (700 MHz, Chloroform-d) δ 8.07-7.97 (m, 2H, Ar), 7.84-6.84 (m, 101H, Ar), 5.68 (d, J=3.5 Hz, 1H, H-1c), 5.17 (d, J=3.5 Hz, 1H, H-1a), 5.16-5.02 (m, 4H, ArCH), 4.99-4.95 (m, 3H, H-1b, 2×ArCH), 4.94-4.85 (m, 6H), 4.81 (m, 2H, H-1d, ArCH), 4.77-4.64 (m, 9H), 4.63-4.58 (m, 6H, H-1e), 4.56-4.46 (m, 5H), 4.46-4.38 (m, 8H), 4.33 (dd, J=12.1, 3.1 Hz, 1H), 4.28-4.15 (m, 5H), 4.08-3.99 (m, 3H), 3.98-3.92 (m, 2H), 3.92-3.86 (m, 3H), 3.85-3.78 (m, 3H), 3.77-3.67 (m, 4H), 3.66-3.57 (m, 4H), 3.50 (dd, J=9.6, 3.4 Hz, 1H, H-2b), 3.49-3.44 (m, 2H, H-2c, H-6b), 3.41 (dd, J=9.4, 3.5 Hz, 1H, H-2a), 3.29-3.06 (m, 3H, OCH$_2$, NCH$_2$), 1.86 (s, 3H, OAc), 1.52-1.36 (m, 4H, CH$_2$CH$_2$), 1.22-1.04 (m, 2H, CH$_2$); $^{13}$C NMR (176 MHz, CDCl$_3$) δ 170.6, 166.1, 138.9, 138.8, 138.8, 138.7, 138.6, 138.5, 138.3, 138.0, 137.7, 136.7, 136.5, 136.0, 136.0, 133.3, 133.3, 133.2, 133.0, 133.0, 132.9, 132.8, 132.8, 130.0, 129.6, 128.6, 128.5, 128.5, 128.4, 128.4, 128.3, 128.3, 128.2, 128.2, 128.1, 128.1, 128.1, 128.0, 128.0, 127.9, 127.9, 127.9, 127.9, 127.8, 127.8, 127.7, 127.7, 127.6, 127.6, 127.6, 127.5, 127.5, 127.5, 127.4, 127.4, 127.4, 127.3, 127.3, 127.1, 127.0, 126.9, 126.6, 126.3, 126.2, 126.1, 126.0, 126.0, 126.0, 125.9, 125.9, 125.8, 125.7, 125.6, 125.6, 125.6, 125.5, 125.5, 97.3 (C-1a, C-1e), 97.2 (C-1b), 96.4 (C-1d), 95.7 (C-1c), 84.6, 82.1, 81.7, 81.7, 80.7, 80.6, 80.4, 79.4, 77.8, 76.5, 75.8, 75.5, 75.4, 75.1, 74.8, 74.7, 74.6, 73.2, 72.6, 72.5, 71.9, 71.9, 71.8, 71.7, 71.5, 70.9, 70.9, 68.8, 67.8, 67.1, 66.1, 65.4, 64.4, 63.3, 50.5, 50.2, 47.1, 46.1, 29.2, 28.0, 27.5, 23.4, 20.9. HRMS (ESI) m/z calcd for C$_{187}$H$_{187}$NO$_{31}$Na$_2$ [M+2Na]$^{2+}$ 3030.2977, found 1515.1508.

Compound 39:

The compound 38 (126 mg) was dissolved in DCM/MeOH (1/1, v/v, 2.6 mL) and cooled to 0° C. AcCl (0.26 mL) was added. The reaction solution was reacted at room temperature for 24 h. After the completion of reaction, the reaction solution was diluted with DCM and washed with NaHCO$_3$. The organic phase was dried over anhydrous Na$_2$SO$_4$, separated and purified by column chromatography to obtain a compound 39 (101 mg, 82%). [α]$^{22}_D$=39.5 (c 0.9, CH$_3$Cl). $^1$H NMR (700 MHz, Chloroform-d) δ 8.01 (d, J=7.8 Hz, 2H), 7.84-6.78 (m, 101H), 5.72 (d, J=3.4 Hz, 1H, H-1c), 5.18 (d, J=3.4 Hz, 2H, H-1a, ArCH), 5.18-5.12 (m, 2H), 5.09-5.02 (m, 3H, H-1b, 2×ArCH), 5.00-4.87 (m, 7H), 4.87-4.78 (m, 3H, H-1d, 2×ArCH), 4.76-4.54 (m, 15H, H-1e), 4.51-4.40 (m, 11H), 4.39-4.27 (m, 3H), 4.27-4.15 (m, 3H), 4.12-4.02 (m, 3H), 3.98-3.72 (m, 14H), 3.71-3.52 (m, 8H), 3.48-3.41 (m, 2H), 3.29-3.06 (m, 3H, OCH$_2$, NCH$_2$), 1.52-1.35 (m, 4H, CH$_2$CH$_2$), 1.23-1.05 (m, 2H, CH$_2$); $^{13}$C NMR (176 MHz, CDCl$_3$) δ 192.4, 192.3, 166.2, 156.7, 156.2, 139.0, 138.7, 138.7, 138.6, 138.6, 138.5, 138.1, 138.0, 137.9, 137.7, 136.9, 136.7, 136.5, 136.5, 136.1, 136.0, 134.6, 134.5, 133.4, 133.3, 133.3, 133.2, 133.1, 133.0, 132.9, 132.9, 132.8, 132.7, 130.0, 129.8, 129.7, 129.6, 129.1, 129.0, 128.6, 128.6, 128.5, 128.5, 128.4, 128.4, 128.4, 128.3, 128.3, 128.3, 128.3, 128.2, 128.2, 128.2, 128.1, 128.0, 128.0, 127.9, 127.9, 127.8, 127.8, 127.8, 127.7, 127.7, 127.6, 127.6, 127.6, 127.6, 127.5, 127.5, 127.5, 127.4, 127.4, 127.3, 127.3, 127.2, 127.2, 127.2, 127.1, 127.1, 127.0, 127.0, 126.6, 126.4, 126.3, 126.1, 126.1, 126.0, 126.0, 125.9, 125.9, 125.9, 125.8, 125.8, 125.7, 125.7, 125.6, 125.5, 122.8, 97.4 (C-1a, C-1e), 97.2 (C-1b), 96.6 (C-1d), 95.7 (C-1c), 84.7, 82.0, 81.7, 81.7, 80.7, 80.5, 80.4, 79.4, 78.7, 78.1, 77.7, 77.4, 77.3, 75.9, 75.5, 75.5, 75.3, 75.2, 74.9, 74.8, 74.8, 74.7, 73.2, 72.7, 72.5, 72.1, 71.9, 71.9, 71.8, 71.8, 71.5, 71.0, 70.9, 68.9, 67.7, 67.2, 66.1, 65.4, 63.2, 61.8, 50.5, 50.2, 47.1, 46.2, 29.3, 28.0, 27.5, 23.4. HRMS (ESI) m/z calcd for C$_{189}$H$_{189}$NO$_{32}$Na [M+Na]$^+$ 2965.2979, found 2965.2993.

Embodiment 7

Figure 6:
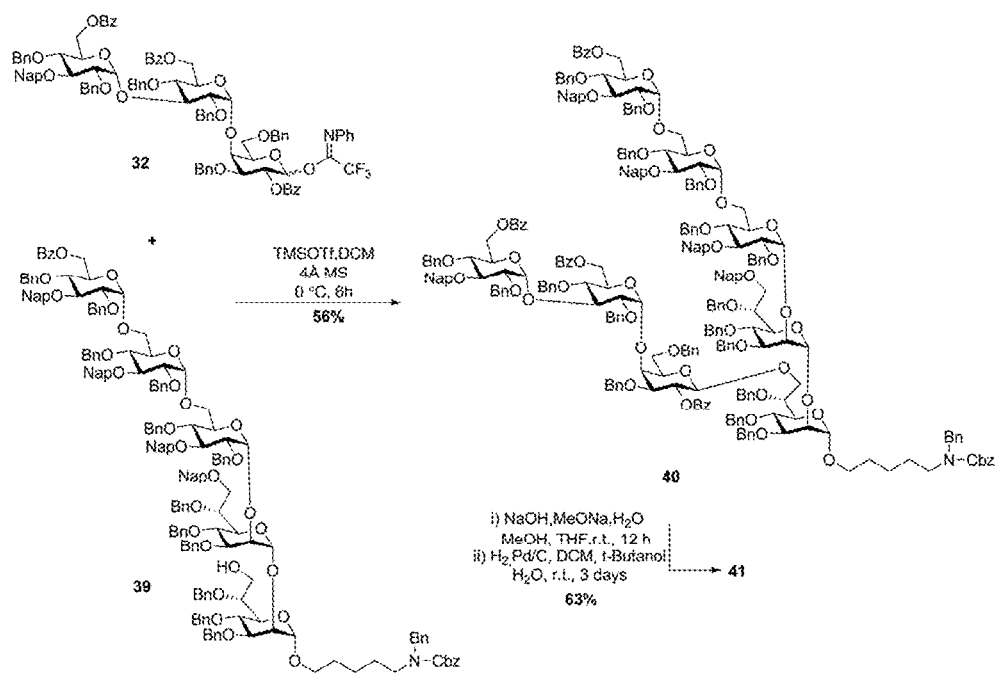
FIG. 6: Synthesis of target octasaccharide 41.

The synthesis route of the target octasaccharide 41 is shown in FIG. 6.

Specific test operations and steps are as follows.

Compound 40:

A trisaccharide donor 32 (38.0 mg, 0.015 mmol) and a pentasaccharide acceptor 39 (29.4 mg, 0.01 mmol) were co-distilled three times with toluene. Dry DCM (1.0 mL) and an activated 4 Å molecular sieve were added. The solution was stirred at room temperature for 30 min and then cooled to 0° C. TMSOTf (0.05 M in DCM, 30 uL, 1.5 umol) was added and the reaction solution was stirred at 0° C. for 6 h. After the completion of reaction, the reaction was terminated with pyridine. The reaction solution was filtered, diluted with DCM, then washed with saturated NaHCO$_3$, dried over anhydrous Na$_2$SO$_4$, concentrated, separated and purified by column chromatography to obtain a compound 40 (24.8 mg, 56%). [α]$^{22}_D$=62.8 (c 1.0, CH$_3$Cl). $^1$H NMR (700 MHz, Chloroform-d) δ 8.06-7.86 (m, 8H), 7.83-6.88 (m, 145H), 5.60 (d, J=3.4 Hz, 1H, H-1c), 5.58 (m, 2H, H-1h, H-2f), 5.10 (m, 2H), 5.07 (d, J=3.8 Hz, 2H, H-1a, H-1g), 5.07-4.98 (m, 6H), 4.98-4.87 (m, 10H, H-1b), 4.87-4.81 (m, 2H), 4.80-4.72 (m, 4H, H-1d), 4.72-4.62 (m, 11H), 4.62-4.48 (m, 18H, H-1e), 4.48-4.26 (m, 26H, H-1f), 4.25-4.17 (m, 8H), 4.16-4.10 (m, 3H), 4.09-4.01 (m, 3H), 4.01-3.92 (m, 5H), 3.93-3.84 (m, 5H), 3.82-3.64 (m, 7H), 3.63-3.45 (m, 12H), 3.45-3.29 (m, 6H), 3.25-2.93 (m, 3H, OCH$_2$, NCH$_2$), 1.41-1.31 (m, 2H, CH$_2$), 1.24-1.14 (m, 2H, CH$_2$), 1.09-0.88 (m, 2H, CH$_2$). $^{13}$C NMR (176 MHz, CDCl$_3$) δ 166.1, 166.0, 165.0, 139.4, 139.0, 138.9, 138.9, 138.8, 138.7, 138.7, 138.6, 138.4, 138.2, 138.1, 138.1, 138.0, 138.0, 137.7, 137.6, 137.4, 136.9, 136.5, 136.4, 136.1, 136.1, 136.0, 133.4, 133.3, 133.3, 133.3, 133.1, 133.0, 133.0, 132.9, 132.9, 132.9, 132.8, 132.7, 130.3, 130.2, 130.2, 130.1, 129.9, 129.8, 129.7, 129.7, 129.6, 129.0, 129.0, 128.7, 128.6, 128.6, 128.5, 128.5, 128.4, 128.4, 128.4, 128.4, 128.3, 128.3, 128.3, 128.3, 128.3, 128.2, 128.2, 128.1, 128.1, 128.0, 128.0, 128.0, 127.9, 127.9, 127.9, 127.9, 127.8, 127.7, 127.7, 127.7, 127.6, 127.6, 127.6, 127.6, 127.5, 127.5, 127.4, 127.4, 127.4, 127.3, 127.3, 127.2, 127.2, 127.1, 127.1, 126.9, 126.9, 126.8, 126.7, 126.6, 126.4, 126.4, 126.4, 126.1, 126.1, 126.1, 126.0, 126.0, 125.9, 125.9, 125.8, 125.8, 125.7, 125.7, 125.6, 102.1 (C-1f), 98.4 (C-1a, C-1g), 97.7 (C-1b), 97.2 (C-1e), 97.1

(C-1h), 96.1 (C-1c, C-1d), 84.3, 82.5, 82.2, 81.9, 81.7, 80.8, 80.5, 80.4, 80.3, 80.2, 79.3, 79.1, 78.5, 78.4, 77.9, 76.6, 76.1, 75.8, 75.8, 75.6, 75.6, 75.1, 75.1, 74.9, 74.6, 74.3, 74.2, 73.6, 73.5, 73.3, 73.3, 73.1, 72.7, 72.6, 72.5, 71.9, 71.7, 71.7, 71.6, 71.4, 70.8, 70.2, 69.0, 68.8, 68.6, 67.8, 67.6, 67.1, 65.6, 63.4, 63.3, 63.2, 50.5, 50.1, 47.1, 46.2, 44.8, 32.0, 29.7, 29.5, 29.4, 29.1, 27.9, 27.5, 23.2, 22.7. The $J_{C-H}$ coupling constants were 176.4 Hz (c), 174.4 Hz (h), 170.0 Hz (a), 170.4 Hz (g), 170.4 Hz (b), 168.8 Hz (d), 170.4 Hz (e), 163.6 Hz (f). HRMS (ESI) m/z calcd for $C_{279}H_{273}NO_{49}Na_2$ [M+2Na]$^{2+}$ 4466.8686, found 2233.4497.

Compound 41:

The compound 41 is a structure of Formula I, wherein $R_n$ are all H. The compound 40 (10 mg, 2.3 ummol) was dissolved in MeOH/THF (1:1, v/v, 1 mL). 15% NaOH (100 uL) was added and was stirred for 1 h. MeONa (50 mg) was added. The solution was stirred at room temperature for 12 h, and the reaction solution was neutralized to pH 7 by adding Amberlite IR120 H$^+$ resin. The solution was filtered, concentrated, separated and purified by column chromatography to obtain a semi-deprotected product. The semi-deprotected product was dissolved in DCM/t-Butanol/H 2 O (3:6:1, v/v/v, 2 mL) and Pd/C was added. The mixture was reacted for three days under H$_2$ pressure at 1 atmosphere, and was filtered, concentrated, and purified on a C18 reverse phase column to obtain a completely deprotected product 41 (2.1 mg, 63%). $^1$H NMR (700 MHz, D$_2$O) δ5.37 (d, J=3.7 Hz, 1H, H-1c), 5.35 (d, J=3.9 Hz, 1H, H-1f), 5.02 (d, J=3.7 Hz, 1H, H-1a), 4.99 (d, J=3.7 Hz, 1H, H-1g), 4.96 (s, 1H, H-1d), 4.95 (d, J=3.9 Hz, 1H, H-1h), 4.79 (s, 1H, H-1e), 4.52 (d, J=7.8 Hz, 1H, H-1f), 4.24 (d, J=2.9 Hz, 1H), 4.23-4.16 (m, 3H), 4.13-4.08 (m, 2H), 4.08-4.01 (m, 4H), 3.99 (dt, J=10.2, 3.2 Hz, 1H), 3.95-3.90 (m, 2H), 3.89-3.67 (m, 25H), 3.67-3.59 (m, 4H), 3.59-3.52 (m, 7H), 3.51-3.41 (m, 3H), 3.02 (t, J=7.6 Hz, 2H), 1.74-1.62 (m, 4H), 1.52-1.42 (m, 2H). $^{13}$C NMR (176 MHz, D$_2$O) δ103.6, 100.1, 99.5, 99.1, 98.7, 97.8, 97.7, 97.4, 80.0, 76.9, 76.8, 76.4, 75.2, 74.0, 73.4, 73.1, 73.0, 72.6, 72.1, 72.1, 72.0, 71.8, 71.7, 71.6, 71.5, 71.5, 70.9, 70.8, 70.7, 70.7, 70.5, 70.4, 70.3, 69.7, 69.5, 69.4, 69.2, 69.2, 68.0, 67.7, 67.6, 65.2, 62.5, 61.8, 60.5, 60.2, 60.0, 59.8, 39.4, 28.0, 26.6, 22.5. HRMS (ESI) m/z calcd for $C_{55}H_{97}NO_{43}Na$ [M+H]$^+$ 1460.5507, found 1460.547.

What is claimed is:

1. An outer core octasaccharide of *Helicobacter pylori* or a derivative thereof, as shown in a Formula I:

Formula I

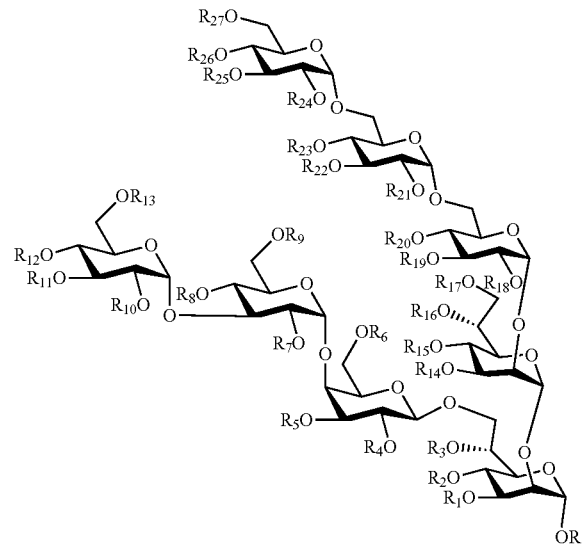

wherein R is —(CH$_2$)$_n$—N—Y$_1$Y$_2$ or —(CH$_2$)$_n$—N—Y$_1$Y$_2$ (linker), n=1-10, N is nitrogen, Y$_1$ is H or benzyl (Bn), Y$_2$ is H or carbobenzoxy (Cbz); wherein R$_1$, R$_2$, R$_3$, R$_6$, R$_7$, R$_8$, R$_{10}$, R$_{12}$, R$_{14}$, R$_{15}$, R$_{16}$, R$_{18}$, R$_{20}$, R$_{21}$, R$_{23}$, R$_{24}$, and R$_{26}$ are H or benzyl (Bn); wherein R$_5$, R$_{11}$, R$_{17}$, R$_{19}$, R$_{22}$, and R$_{25}$ is H or 2-naphthylmethyl (Nap); and wherein R$_4$, R$_9$, R$_{13}$, and R$_{27}$ are ester groups.

2. A method of synthesizing the outer core octasaccharide of *Helicobacter pylori* according to claim 1, comprising the following steps:

step 1, synthesizing required monosaccharide building blocks A, B, C, and D:

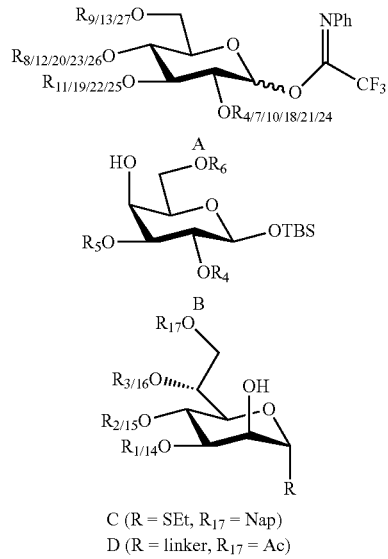

wherein R is —(CH$_2$)$_n$—N—Y$_1$Y$_2$ or —(CH$_2$)$_n$—N—Y$_1$Y$_2$ (linker), n=1-10, N is nitrogen, Y$_1$ is benzyl (Bn), Y$_2$ is carbobenzoxy (Cbz); wherein R$_1$, R$_2$, R$_3$, R$_6$, R$_7$, R$_8$, R$_{10}$, R$_{12}$, R$_{14}$, R$_{15}$, R$_{16}$, R$_{18}$, R$_{20}$, R$_{21}$, R$_{23}$, R$_{24}$, and R$_{26}$ are benzyl (Bn); wherein R$_5$, R$_{11}$, R$_{17}$, R$_{19}$, R$_{22}$, and R$_{25}$ is 2-naphthylmethyl (Nap); and wherein R$_4$, R$_9$, R$_{13}$, and R$_{27}$ are ester groups;

step 2, assembling protected octasaccharide by a glycosylation reaction; and step 3, deprotecting the octasaccharide.

3. The method according to claim 2, wherein in step 1, when the monosaccharide building blocks A, B, C, and D are synthesized, the solvent used is one or more of dry dichloromethane, ethyl acetate, methanol, N,N-dimethylformamide, tetrahydrofuran, pyridine, chloroform, and 80% acetic acid aqueous solution; wherein a substrate concentration is 0.02-0.5 M; wherein an acid as a reagent or catalyst is hydrochloric acid, acetic acid or p-toluenesulfonic acid; wherein a reaction temperature is −78° C. to reflux temperature of the solvent; and wherein a reaction time is 1-48 h.

4. The method according to claim 2, wherein step 2 comprises (1) assembly of a trisaccharide donor, (2) assembly of a pentasaccharide acceptor, and (3) assembly of a fully protected octasaccharide;

wherein, the assembly conditions of the trisaccharide donor are that a substrate is sugar building blocks A and B, and a reaction solvent is Et$_2$O/DCM; adding thiophenein an amount of 10 equivalents of donor, and using a desiccant; wherein a reaction temperature is 0° C. to room temperature, and reaction process is under inert gas protection; wherein after reaction materials disappear, quenching reaction with pyridine or triethylamine, filtering, washing, extracting and drying are carried out, and purifying a product by a silica gel column;

wherein the assembly conditions of the pentasaccharide acceptor are that the substrate is sugar building blocks A, C, and D, and the reaction solvent is $Et_2O$/DCM or DCM; adding thiophene in an amount of 10 equivalents of donor, and using a desiccant; wherein a reaction temperature is 0° C. to room temperature, and a reaction process is under inert gas protection;

wherein after reaction materials disappear, quenching reaction with pyridine or triethylamine, filtering, washing, extracting and drying are carried out, and purifying a product by a silica gel column; and wherein the assembly conditions of the octasaccharide is that the substrate is the above trisaccharide donor and the pentasaccharide acceptor, and organic solvent for glycosidation is dry dichloromethane or dry diethyl either or both; wherein glycosylation reaction is carried out under the action of Lewis acid to obtain the protected octasaccharide; wherein after reaction materials disappear, quenching with pyridine or triethylamine, filtering, washing, extracting and drying are carried out, and purifying product by a silica gel column.

5. The method according to claim 4, wherein,
the desiccant is one or more of 3 Å molecular sieve, 4 Å molecular sieve, 5 Å molecular sieve, anhydrous sodium sulfate, anhydrous magnesium sulfate, and anhydrous calcium sulfate;
wherein mass ratio of the desiccant to a reactant is 1.0 to 4.0;
wherein the inert gas is nitrogen or argon;
wherein the Lewis acid is TMSOTf, TfOH, or AgOTf, and for the reaction of thioglycoside, NIS is additionally added as a promoter together with Lewis acid.

6. The method according to claim 4, wherein substrate concentration during the glycosylation reaction is 0.01 M to 0.1 M, the reaction temperature is −50° C. to 0° C. to room temperature; wherein the room temperature is 20-30° C.; and reaction time is 1 h to 7 h.

7. The method according to claim 5, wherein substrate concentration during the glycosylation reaction is 0.01 M to 0.1 M, the reaction temperature is −50° C. to 0° C. to room temperature; wherein the room temperature is 20-30° C.; and reaction time is 1 h to 7 h.

8. The method according to claim 2, wherein in step 3, the acyl of the protected octasaccharide is removed under alkaline conditions, and solvent used is one or more of methanol, tetrahydrofuran, and dichloromethane; and wherein after completion of reaction, the reaction is neutralized with $H^+$ resin, reaction temperature is room temperature, and the reaction time is 2 h to 12 h to obtain a semi-deprotected octasaccharide.

9. The method according to claim 8, wherein in step 3, the semi-deprotected octasaccharide is completely deprotected by using palladium carbon and hydrogen, and solvent used is one or more of tetrahydrofuran, dichloromethane, ethyl acetate, tert-butanol, water, methanol, and acetic acid; wherein the palladium carbon is 10% palladium carbon; wherein mass ratio of palladium carbon to the reactant is 0.1:1-0.5:1; wherein hydrogen pressure for debenzylation and 2-naphthylmethyl removal is 1-100 atm; and wherein the reaction temperature is normal temperature, and reaction time is 1-48 h.

10. A *Helicobacter Pylori* vaccine, comprising the outer core octasaccharide of *Helicobacter Pylori* according to claim 1, which services as the epitope.

11. A method for producing a α-glycosidic bond of glucose, comprising co-distilling glycosyl donor and acceptor for 2 to 3 times in toluene, adding dry DCM or DCM/$Et_2O$ in a volume ratio of 1:2; wherein substrate concentration is 0.01-0.1 M, and the activated 3 Å or 4 Å molecular sieve is used as a desiccant; adding thiophene in an amount of 10 equivalents of glycosyl donor; stirring reaction at room temperature for 20-30 min, then cooling to −50-0° C.; adding TMSOTf as a promotor, and carrying reaction time for 1-7 h; and terming reaction with pyridine.

* * * * *